(12) United States Patent
Jabbari

(10) Patent No.: US 10,494,610 B2
(45) Date of Patent: Dec. 3, 2019

(54) THREE DIMENSIONAL MATRIX FOR CANCER STEM CELLS

(71) Applicant: UNIVERSITY OF SOUTH CAROLINA, Columbia, SC (US)

(72) Inventor: Esmaiel Jabbari, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/205,489

(22) Filed: Nov. 30, 2018

(65) Prior Publication Data

US 2019/0085298 A1    Mar. 21, 2019

Related U.S. Application Data

(62) Division of application No. 14/527,028, filed on Oct. 29, 2014, now Pat. No. 10,227,566.

(60) Provisional application No. 61/962,057, filed on Oct. 30, 2013, provisional application No. 61/962,056, filed on Oct. 30, 2013.

(51) Int. Cl.
*C12N 5/095* (2010.01)

(52) U.S. Cl.
CPC ........ *C12N 5/0695* (2013.01); *C12N 2533/30* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 7,374,774 B2 | 5/2008 | Bowlin et al. | |
| 7,531,503 B2 | 5/2009 | Atala et al. | |
| 7,737,131 B2 | 6/2010 | Kiick et al. | |
| 7,759,082 B2 | 7/2010 | Bowlin et al. | |
| 7,767,221 B2 | 8/2010 | Lu et al. | |
| 8,066,932 B2 | 11/2011 | Xu | |
| 8,071,722 B2 | 12/2011 | Kaplan et al. | |
| 8,202,551 B2 | 6/2012 | Li et al. | |
| 8,267,992 B2 | 9/2012 | Atanasoska et al. | |
| 8,449,622 B2 | 5/2013 | McKay | |
| 8,551,390 B2 | 10/2013 | Jun et al. | |
| 8,586,345 B2 | 11/2013 | Simpson et al. | |
| 8,691,543 B2 | 4/2014 | Gaudette et al. | |
| 10,227,566 B2 * | 3/2019 | Jabbari | C12N 5/0695 |
| 2003/0215624 A1 | 11/2003 | Layman et al. | |
| 2004/0229333 A1 | 11/2004 | Bowlin et al. | |
| 2006/0067969 A1 | 3/2006 | Lu et al. | |
| 2006/0182685 A1 * | 8/2006 | Bishai | C12Q 1/02 424/9.2 |
| 2006/0204445 A1 | 9/2006 | Atala et al. | |
| 2006/0204539 A1 | 9/2006 | Atala et al. | |
| 2007/0269481 A1 | 11/2007 | Li et al. | |
| 2008/0038352 A1 | 2/2008 | Simpson et al. | |
| 2008/0102145 A1 | 5/2008 | Kim et al. | |
| 2008/0109070 A1 | 5/2008 | Wagner et al. | |
| 2008/0159985 A1 | 7/2008 | Bowlin et al. | |
| 2008/0213389 A1 | 9/2008 | Lelkes et al. | |
| 2008/0220042 A1 | 9/2008 | Hashi et al. | |
| 2008/0220054 A1 | 9/2008 | Shastri et al. | |
| 2010/0047309 A1 | 2/2010 | Lu et al. | |
| 2013/0338791 A1 | 12/2013 | McCullen et al. | |

OTHER PUBLICATIONS

Fu et al. (Biomaterials 33 (2012) 48-58) (Year: 2012).*
Kwack et al. (The FASEB Journal. 2008;22:819.6, abstract only) (Year: 2008).*
EsiBio (downloaded on Feb. 8, 2018 from URL:<http://www.esibio.com/pegda/>) (Year: 2018).*
Yang et al. (Abstract LB-492, DOI: 10.1158/1538-7445.AM2012-LB-492, Apr. 15, 2012) (Year: 2012).*
Kim et al. (Lab Anim Res 2011:27(2), 147-152) (Year: 2011).*
Yip et al. (Biochemical and Biophysical Research Communications 433 (2013) 327-332) (Year: 2013).*
Arai, et al. "Tie2/Angiopoietin-1 Signaling Regulates Hematopoietic Stem Cell Quiescence in the Bone Marrow Niche" *Cell*, 118 (2004) pp. 149-161.
Bryant, et al. "Hydrogel properties influence ECM production by chondrocytes photoencapsulated in poly(ethylene glycol) hydrogels" *Jnl. Biomed Mater Res.* 59 (2002) pp. 63-72.
Buxton, et al. "Design and Characterization of Poly(Ethylene Glycol) Photopolymerizable Semi-Interpenetrating Networks for Chondrogenesis of Human Mesenchymal Stem Cells" *Tissue Engineering* 13 (2007) pp. 2549-2560.
Chen, et al. "Geometric Control of Cell Life and Death" *Science* 276 (1997) pp. 1425-1428.
Chirila, et al. "Poly(2-hydroxyethyl methacrylate) sponges as implant materials: in vivo and in vitro evaluation of cellular invasion" *Biomaterials.* 14(1) (1993) pp. 26-38.
Dawson, et al. "Biomaterials for stem cell differentiation" *Adv. Drug Deliv. Reviews* 60 (2008) pp. 215-228.
Debnath, et al. "Modelling Glandular Epithelial Cancers in Three-Dimensional Cultures" *Nature Reviews—Cancer* 5 (2005) pp. 675-688.
Discher, et al. "Tissue Cells Feel and Respond to the Stiffness of Their Substrate" *Science* 310, (2005) pp. 1139-1144.

(Continued)

*Primary Examiner* — Sergio Coffa
(74) *Attorney, Agent, or Firm* — Dority & Manning, P.A.

(57) ABSTRACT

Synthetic inert 3D gel culture systems are described that can be finely tuned to exhibit desired and predetermined physical, chemical, mechanical, and biochemical properties. The culture system can be utilized to study the effect of microenvironmental factors on cancer cell response, and in particular on cancer stem cell (CSC) response. Cancer cells can be encapsulated in a crosslinked gel system having a narrow range of predetermined gel stiffness. One or more biochemical factors including peptides that can affect the growth, development, and/or proliferation of CSCs can be incorporated in the system to examine the effects of the factor(s) on the encapsulated cells with regard to growth, proliferation, size, etc.

18 Claims, 15 Drawing Sheets

Specification includes a Sequence Listing.

(56) References Cited

OTHER PUBLICATIONS

Doroski, et al. "Cyclic Tensile Culture Promotes Fibroblastic Differentiation of Marrow Stromal Cells Encapsulated in Poly(Ethylene Glycol)-Based Hydrogels" *Tissue Engineering: Part A* 16 (2010) pp. 3457-3466.
Elisseeff, et al. "Photoencapsulation of chondrocytes in poly(ethylene oxide)-based semi-interpenetrating networks" *J. Biomed Mater Res.* 51 (2000) pp. 164-171.
Engler, et al. "Embryonic cardiomyocytes beat best on a matrix with heart-like elasticity: scar-like rigidity inhibits beating" *Jnl. of Cell Sci.* 121 (2008) pp. 3794-3802.
Engler, et al. "Extracellular matrix elasticity directs stem cell differentiation" *J. Musculoskelet Neuronal Interact* 7(4) (2007) p. 335.
Engler, et al. "Matrix Elasticity Directs Stem Cell Lineage Specification" *Cell* 126 (2006) pp. 677-689.
He, et al. "Cellular and Molecular Regulation of hematopoietic and Intestinal Stem Cell Behavior" *Ann. N.Y. Acad. Sci.* 1049 (2005) pp. 28-38.
Huebsch, et al. "Harnessing traction-mediated manipulation of the cell/matrix interface to control stem-cell fate" *Nature Materials* 9 (2010) pp. 518-526.
Keung, et al. "Presentation Counts: Microenvironmental Regulation of Stem Cells by Biophysical and Material Cues" *Annu. Rev. Cell Dev. Biol.* 26 (2010) pp. 533-556.
Lee, et al. "Gel microstructure regulates proliferation and differentiation of MC3T3-El cells encapsulated in alginate beads" *Acta Biomaterialia* 8 (2012) pp. 1693-1702.
Liu, et al. "Biomimetic hydrogels for chondrogenic differentiation of human mesenchymal stem cells to neocartilage" *Biomaterials* 31 (2010) pp. 7298-7307.
Masters, et al. "Designing scaffolds for valvular interstitial cells: Cell adhesion and function on naturally derived materials" *Wiley Periodicals, Inc.* (2004) pp. 172-180.
Nemir, et al. "Synthetic Materials in the Study or Cell Response to Substrate Rigidity" *Annals of Biomedical Engineering Society* 38(1) (2009) pp. 2-20.
Pampaloni, et al. "The third dimension bridges the gap between cell culture and live tissue," *Nature Reviews Molecular Cell Biology* 8 (2007) pp. 839-845.
Papadopoulos, et al. "Injectable and photopolymerizable Tissue-Engineered Auricular Cartilage Using Poly(Ethylene Glycol) Dimethacrylate Copolymer Hydrogels" *Tissue Engineering: Part A* 17(1-2) (2011) pp. 161-169.
Parekh, et al. "Modulus-driven differentiation of marrow stromal cells in 3D scaffolds that is independent of myosin-based cytoskeletal tension" *Biomaterials* 32 (2011) pp. 2256-2264.
Pek, et al. "The effect of matrix stiffness on mesenchymal stem cell differentiation n a 3D thixotropic gel" *Biomaterials* 31 (2010) pp. 385-391.
Provenzano, et al. "Matrix density-induced mechanoregulation of breast cell phenotype, signaling and gene expression through a FAK-ERK linkage" *Oncogene* 28 (2009) pp. 4326-4343.
Raof, et al. "Bioengineering embryonic stem cell microenvironments for exploring inhibitory effects on metastatic breast cancer cells" *Biomaterials* 32 (2011) pp. 4130-4139.
Rehfeldt, et al. "Cell responses to the mechanochemical microenvironment—Implications for regenerative medicine and drug delivery" *Adv. Drug Deliv. Reviews* 59 (2007) pp. 1329-1339.
Sawhney, et al. "Interfacial photopolymerization of poly(ethylene glycol)-based hydrogels upon alginate-poly (l-lysine) microcapsules for enhanced biocompatibility" *Biomaterials* 14(13) (1993) pp. 1008-1016.
Schrader, et al. "Matrix Stiffness Modulates Proliferation, Chemotherapeutic Response, and Dormancy in Hepatocellular Carcinoma Cells" *Hepatology* 53(4) (2011) pp. 1192-1205.
Smith, et al. "Three-Dimensional Culture of Mouse Renal Carcinoma Cells in Agarose Macrobeads Selects for a Subpopulation of Cells with Cancer Stem Cell or Cancer Progenitor Properties" *Cancer Res.* 71(3) (2011) pp. 716-724.
Sun, et al. "Forcing Stem Cells to Behave: A Biophysical Perspective of the Cellular Microenvironment" *Annu. Rev. Biophys.* 41 (2012) pp. 519-542.
Tilghman, et al. "Matrix Rigidity Regulates Cancer Cell Growth and Cellular Phenotype" *PLoS One* 5(9) (2010) e12905: pp. 1-13.
Yang, et al. "Effect of CD44 Binding Peptide Conjugated to an Engineered Inert Matrix on Maintenance of Breast Cancer Stem Cells and Tumorsphere Formation" *PLoS One* 8(3) (2013) e59147: pp. 1-15. (Abstract only).
Yang, et al. "Three-Dimensional-Engineered Matrix to Study Cancer Stem Cells and Tumorsphere Formation: Effect of Matrix Modulus" *Tissue Engineering Part A* 19(5-6) (2013) pp. 669-685.
Zaman, et al. "Migration of tumor cells in 3D matrices is governed by matrix stiffness along with cell-matrix adhesion and proteolysis" *PNAS* 103(29) (2006) pp. 10889-10894.

\* cited by examiner

FIG. 1A
FIG. 1B
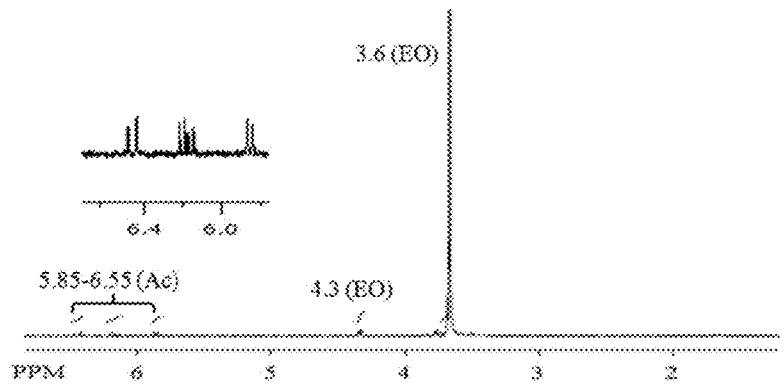
FIG. 1
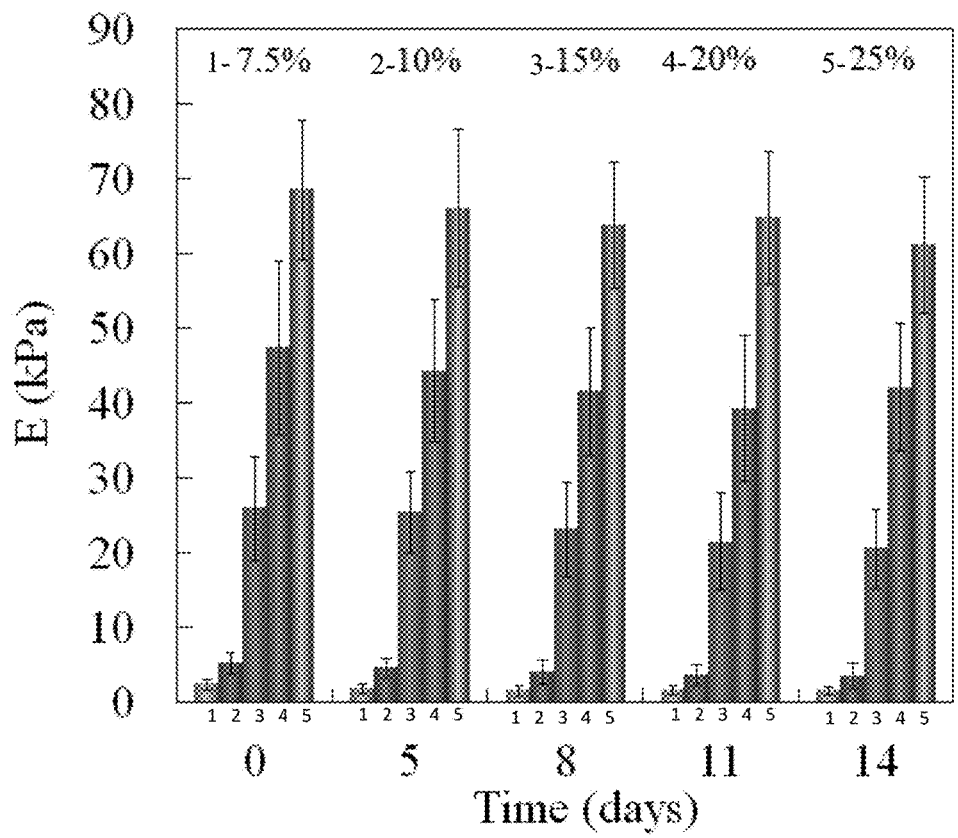
FIG. 2

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catggccttc cgtgttccta                                              20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctgcttcac caccttcttg a                                            21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gaatgtaacc tgccgctacg    20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ggaggtgttg gacgtgac    18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cttctggcac tgctcctacc    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gagagagagc caggagacca    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
agcagcaagg aaagatccaa    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ggaataccga ggctgatgaa    20

-continued

```
<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggacacttc tcacacta                                                 18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagagcaaga gggtctgcag gag                                           23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagtcaacgg atttggtcgt                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgattttgg agggatctcg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggctttcaat agcaccttgc                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acacccctgt gttgtttgct                                               20

<210> SEQ ID NO 15
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccttattg gcctcaggaa                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctgcttgga aggctctatg                                               20

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Leu Val Ser Tyr Asn Gly Ile Ile Phe Phe Leu Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Leu Phe Gly Phe Leu Lys Ile Tyr Ser Arg Ile Asn
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Arg Gly Asp Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Arg Asp Gly Ser
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Gln Pro Pro Arg Ala Arg Ile
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Pro Gln Ile Pro Trp Ala Arg
1               5

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggagcagcag gatcagaatc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggacaggaa cactgcaaat                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggttgatgg tccagtttct                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```
gcttaaaggc agatggcaac                                            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaatggtgat gggagtgagc                                            20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgacatcgag caggtgaaag                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gagtagcaag gccaatgagc                                            20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagtgggcaa ccctgagtat                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggcccttaa atatgccatt                                            20

<210> SEQ ID NO 32
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 32
actgtgaagg gacggtcaac                                                     20
```

THREE DIMENSIONAL MATRIX FOR CANCER STEM CELLS

CROSS REFERENCE TO RELATED APPLICATIONS

This application is a Divisional Application of U.S. patent application Ser. No. 14/527,028, having a filing date of Oct. 29, 2014, now U.S. Pat. No. 10,227,566; which claims filing benefit of U.S. Provisional Patent Application Ser. No. 61/962,057 entitled "Engineered matrix for Enriching Malignant Cancer Stem Cells" having a filing date of Oct. 30, 2013; and U.S. Provisional Patent Application Ser. No. 61/962,056 entitled "Regulating Cancer Stem Cell Maintenance with Integrin and Heparin Binding Peptides" having a filing date of Oct. 30, 2013, all of which are incorporated herein by reference in their entirety.

GOVERNMENT SUPPORT CLAUSE

This invention was made with government support under CBET-0931998, CBET-0756394 and DMR-1049381 awarded by the National Science Foundation and under 1R03DE019180-01A1 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 12, 2014, is named USC-457 (1067)_SL.txt and is 7,517 bytes in size.

BACKGROUND

Breast cancer is the most common cancer among women in industrialized countries. The development of breast cancer is a multiple-step process and regulated by the tumor microenvironment. This development process may take many years and is difficult to follow in vivo. Therefore, there is a need to develop in vitro models to study the molecular basis of tumorigenesis and progression in breast cancer as well as in other cancers.

Most in vitro cancer cell studies use standard two-dimensional (2D) cell culture systems. However, cells grown on 2D tissue culture behave differently from those grown in a physiological three-dimensional (3D) environment due to the lack of proper cell-cell and cell-matrix interactions as well as the lack of gradient of nutrients and growth factors, which are known to play critical roles in cancer initiation, progression and metastasis. For example, when cancer cells are cultured in 2D plates, their malignancy is reduced compared to those under in vivo conditions. Animal models are also frequently used to study molecular pathways and drug response in cancer research. In these cases, either animal tumors grown in syngeneic animals or human tumors grown in immunocompromised animals are used. Therefore, animal models may not adequately reproduce the features of human cancers in vivo.

To bridge the gap between the 2D cell culture system and the in vivo system, the 3D in vitro cell culture system has emerged. In many 3D models, cell lines or cells from dissociated tissues are embedded in 3D matrices and cultured to promote cell-cell interaction, adhesion, migration and in vivo-like morphogenesis. Comparison between 2D and 3D culture systems has revealed significant differences in all aspects of cell behavior from cell shape and growth to gene expression and response to stimuli. Various types of materials have been used to generate a 3D matrix. Type 1 collagen and Matrigel™ are the most widely used matrices because they are biocompatible and support adhesion and growth of many cell types. Alginate and agarose gels are also used as a matrix to study the behavior of cancer cells under 3D conditions. Unfortunately, it is difficult to control the physical characteristics of gels formed of naturally derived polymers. In addition, it is difficult to isolate and study cell response to individual factors in these microenvironments as the naturally derived matrices tend to interact with surface receptors of the cells.

As a result, inert synthetic polymers have been examined for use in development of 3D gels. The use of inert synthetic polymers can provide increased flexibility in designing 3D matrices with a wide range of mechanical, physical, and biological properties. Among the synthetic materials, polyethylene glycol (PEG) hydrogel, due to its inert nature, has been used extensively to form engineered matrices for cell encapsulation. While the development of PEG 3D matrices has been an improvement in the art, room for further improvement exists.

For example, while the effect of matrix stiffness on the response of normal stem cells has been studied, the effect of matrix stiffness on cancer stem cells (CSCs) encapsulated within an inert microenvironment has not been investigated. Normal stem cells and cancer stem cells use similar signaling pathways to maintain their stemness. However, they may respond to the environmental cues differently. The microenvironment or niche under normal conditions inhibits stem cell proliferation and differentiation, but cancer stem cells, due to mutations in the cell, are self-sufficient with respect to proliferation. It has been proposed that the stem cell niche is converted from proliferation inhibitory to one favoring cell proliferation in the case of cancer stem cells. What is needed in the art is a tunable 3D matrix that can be utilized to examine such propositions for further understanding the growth and development of cancer cells, and in particular cancer stem cells, e.g., a 3D matrix that can be utilized to enrich a cell sample in cancer stem cells. For instance, the fraction of CSCs in the population of cancer cells is understood to be at most a few percent, and possibly less than 1%. As a result, drug toxicity tests to date evaluate the response of non-stem-like cancer cells to the chemotherapy agent. Unfortunately, CSC's are the cell fraction responsible for cancer recurrence, relapse, and metastasis and the CSC fraction is the most malignant fraction of cells in the population of cancer cells. Therefore, there is a need to develop technologies and 3D matrices that can be utilized to enrich a cell population in cancer stem cells for study and drug testing.

In addition to the need to develop improved 3D matrices, as cancer cells are affected by many factors in their microenvironment, another major challenge to understanding the growth and development of cancer cells lies in developing methods to isolate the effect of single factors on particular cell types while keeping other factors unchanged. For instance, breast tumors are highly heterogeneous, and cells with self-renewal and highly invasive capacity coexist with cells that are more differentiated and non-invasive. Increasing evidence suggests that the heterogeneity of the tumor tissue is rooted in the existence of CSCs. Therefore, understanding the mechanism of CSC maintenance, and in particular the effect of specific factors on CSC maintenance and enrichment, is critical for breast cancer prevention and treatment.

Cell to cell interactions between stem cells and support cells, interactions between stem cells and extracellular matrix (ECM), the composition of ECM and the physicochemical properties of the environment are all key contributing factors in stem cell maintenance. Many in vitro studies have provided insight on the regulation of CSC fate by the microenvironment. However, these studies have been limited by the nature of the support matrix as well as by the inability to isolate the effect of single factors in a realistic model. Accordingly, what is also needed in the art is a 3D matrix having a highly controlled microenvironment so as to more accurately isolate and determine the effects of particular factors on the growth and development of cancer cells, and in particular, of stem cancer cells.

SUMMARY

According to one embodiment, disclosed is a method of forming a three dimensional hydrogel matrix for supporting a cancer stem cell. For instance, the method can include combining an inert synthetic polymer with a crosslinking agent to form a precursor solution and crosslinking the inert synthetic polymer via the crosslinking agent to form the three dimensional hydrogel matrix. More specifically, the concentration of the crosslinking agent and/or the concentration of the inert synthetic polymer can be predetermined in the precursor solution such that the three dimensional hydrogel matrix has a predetermined elastic modulus. In addition, a method can include conjugating a peptide to the matrix that can effect the growth, development, and/or proliferation of a cancer stem cell. For instance, an integrin binding peptide and/or a CD44 binding peptide can be conjugated to the matrix, either of which can be utilized to prevent the proliferation of CSC's (i.e., "turn off" the CSC's) encapsulated in the matrix. Alternatively, a heparin binding peptide can be conjugated to the matrix, which can be utilized to promote the proliferation of CSC's (i.e., "turn on" the CSC's) in the matrix.

Also disclosed is a three dimensional hydrogel matrix comprising a crosslinked inert synthetic polymer. The hydrogel matrix can also include a peptide conjugated to the matrix, the peptide being one that can affect the growth, development, and/or proliferation of a CSC encapsulated in the matrix. The three dimensional hydrogel matrix has an elastic modulus that is predetermined, for instance less than about 10 kilopascals in one particular embodiment.

Also disclosed are methods of utilizing the three dimensional hydrogel matrices for study of a cell population, for instance a cell population that includes cancer cells and cancer stem cells, optionally in conjunction with other cell types. For example, in one embodiment the three dimensional hydrogel matrix can include an integrin binding peptide (e.g., GRGDS, SEQ ID NO.: 19) or a mutant thereof, or the three dimensional hydrogel matrix can include a CD44 binding peptide (e.g., RLVSYNGIIFFLK, SEQ ID NO.: SEQ ID NO.: 17) or a mutant thereof, and the matrix can be utilized to turn off CSC's in the cell population encapsulated in the matrix. In another embodiment, the hydrogel matrix can include a heparin binding peptide (e.g., WQPPRARI (SEQ ID NO.: 21) or a mutant thereof, and the matrix can be utilized to turn on CSC's in a cell population that is encapsulated in the matrix.

BRIEF DESCRIPTION OF THE FIGURES

FIG. 1 schematically illustrates a reaction scheme for acrylation of a PEG macromer (FIG. 1A) and the $^1$H-NMR spectrum of PEGDA macromer (FIG. 1B). The chemical shifts between 5.85 and 6.55 ppm due to acrylate hydrogens are enlarged in the inset of the NMR spectrum.

FIG. 2 graphically illustrates the effect of macromer concentration on elastic modulus of 4T1 cell loaded (1.4× $10^5$ cells/mL) PEGDA hydrogels with incubation time. Error bars correspond to means±1 SD for n=3.

FIG. 4E1, FIG. 4E2, FIG. 4E3, FIG. 4E4, FIG. 4E5, FIG. 4E6, FIG. 4E7, and FIG. 4E8 on the right show the uniformity of cell seeding and cell viability in successive 90 µm layers in the direction of thickness for 5.3 kPa gel, obtained with a confocal fluorescent microscope.

FIG. 5 illustrates the evolution of tumorsphere formation by 4T1 tumor cells encapsulated in PEGDA hydrogels with elastic modulus of 2.5 kPa (left column), 5.3 kPa (center left column), 47.5 kPa (center right column), and MCF7 tumor cells encapsulated in the 5.3 kPa gel (left column) as a function of incubation time. Rows 1, 2, 3, and 4 correspond to incubation times of 5, 8, 11, and 14 days, respectively. At each time point, encapsulated cells were stained with phalloidin for cytoskeleton and DAPI for nucleus, and imaged with an inverted fluorescent microscope.

FIG. 6 presents representative images of tumorsphere density for 4T1 (left column) and MCF7 (right column) cells encapsulated in PEGDA hydrogels with elastic modulus of 2.5 kPa (first row), 5.3 kPa (second row), 26.1 kPa (third row), and 47.5 kPa (fourth row) after 8 days of incubation. At each time point, encapsulated cells were stained with phalloidin for cytoskeleton and DAPI for nucleus, and imaged with an inverted fluorescent microscope.

FIG. 7 presents average tumorsphere size (FIG. 7A and FIG. 7D), tumorsphere size distribution (FIG. 7B and FIG. 7E), and cell count (FIG. 7C and FIG. 7F) for 4T1 and MCF7 tumor cells encapsulated in PEGDA hydrogels with different elastic moduli and incubated for up to 14 days. Graphs FIG. 7A, FIG. 7B, and FIG. 7C correspond to 4T1 cells and FIG. 7D, FIG. 7E, and FIG. 7F correspond to MCF7 cells. The star indicates statistically significant difference between the test group and all other groups at the same time point (FIG. 7A, FIG. 7C, FIG. 7D, and FIG. 7F) or at the same tumorsphere diameter range (FIG. 7B and FIG. 7E). Error bars correspond to means±1 SD for n=3.

FIG. 8 illustrates BrdU staining of 4T1 tumorspheres formed in suspension culture on low adhesion plates (FIG. 8A and FIG. 8C) and formed by encapsulation in PEGDA hydrogels (FIG. 8B and FIG. 8D). FIG. 8A and FIG. 8B were taken after 8 days of incubation while images FIG. 8C and FIG. 8D were following 14 days. Prior to tumorsphere formation, 4T1 cells were incubated with BrdU for 10 days to achieve stable labeling. The presence of BrdU in the cells was confirmed by immunofluorescent staining. The cell nuclei were stained with DAPI.

DETAILED DESCRIPTION

Figure 3:
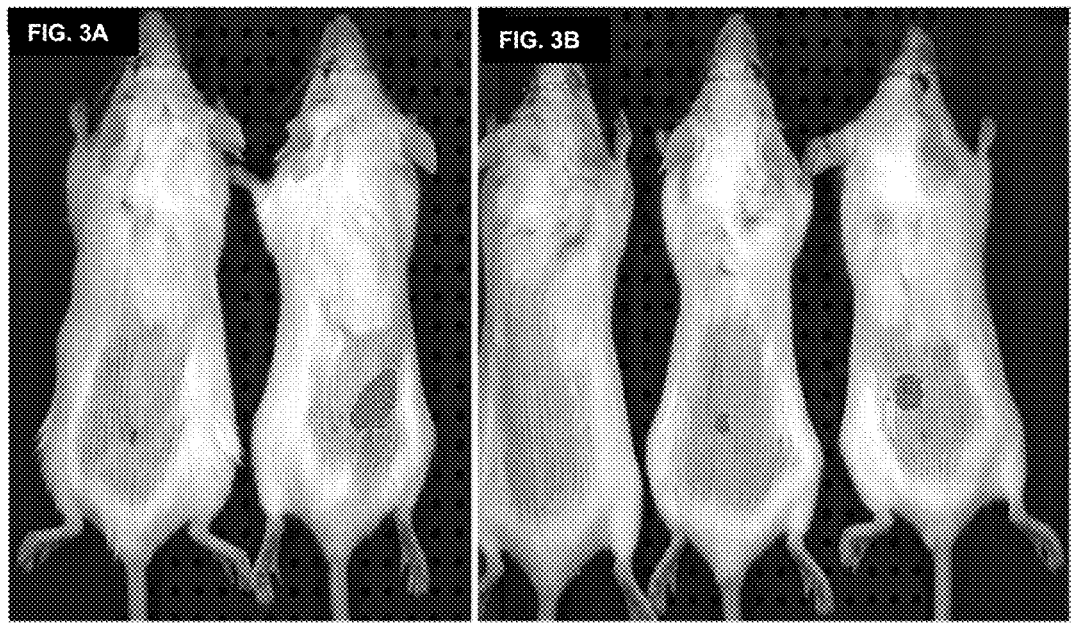
FIG. 3 compares in vivo tumor formation of 4T1 cells from adhesion plates (FIG. 3A) with 4T1 cells from tumorspheres on ultra-low attachment plates (FIG. 3B). The left and right images in FIG. 3A show tumor formation by inoculation of 5000 and 50,000 4T1-Luc cells, respectively. The left, center, and right images in FIG. 3B show tumor formation by inoculation of 500, 1000, and 5000 4T1-luc cells from tumorspheres, respectively. 4T1-Luc cells were inoculated subcutaneously in Balb/c mice. After 1 week, the expression of luciferase in tumors was imaged.

The following description and other modifications and variations to the presently disclosed subject matter may be practiced by those of ordinary skill in the art, without departing from the spirit and scope of the disclosure. In addition, it should be understood that aspects of the various embodiments may be interchanged in whole or in part. Furthermore, those of ordinary skill in the art will appreciate that the following description is by way of example only, and is not intended to limit the invention.

The present disclosure is generally directed to a synthetic inert 3D gel culture system that can be finely tuned to exhibit desired and predetermined physical, chemical, mechanical, and biochemical properties. The culture system can be beneficially utilized to study the effect of microenvironmental factors on cancer cell response and in particular on cancer stem cell (CSC) response. For instance, CSCs formed in a gel system having a narrow range of predetermined gel stiffness following encapsulation of breast cancer cells in the gel can maintain their stemness over time. This effect can be varied by variation in the stiffness of the gel.

As utilized herein, the term 'gel stiffness' and 'matrix stiffness' are utilized interchangeably and generally refer to the elastic modulus of the gel. Determination of elastic modulus of a gel can be carried out according to standard practices, for instance by loading a sample of the gel on the Peltier plate of a rheometer and subjecting the gel to uniaxial compressive force. The slope of the linear fit to the stress-strain curve can be taken as the elastic modulus (E) of the gel.

In addition, the disclosed culture systems can be beneficially utilized to examine the effects of microenvironmental factors on CSCs and on cell populations that are enriched in or alternatively depleted in CSCs. In particular, the synthetic inert 3D gel culture system can be formed to include a peptide that can affect the proliferation of CSCs in a cell population encapsulated in the system. As such, the system can be utilized to better understand the effects of microenvironmental factors such as potential cancer treatment methods and materials on a cell population and in particular on a cancer cell population.

Among the microenvironmental factors of both a 2D and 3D culture system, matrix stiffness is generally known to play an important role in regulating cell function. In vivo, cells have the ability to sense and respond to matrix stiffness by synthesizing the appropriate ECM composition. As the mechanical properties and composition of hard and soft tissues differ significantly, cells need to respond appropriately to environmental cues such as matrix stiffness for survival. Likewise, the proliferation, differentiation, migration, and apoptosis of cancerous cells in the tumor tissue are regulated by microenvironmental factors including matrix stiffness.

In the disclosed 3D culture systems, control of the elastic modulus of the matrix can be utilized to better understand and direct differentiation of encapsulated cells as well as to shift the balance of cell proliferation and apoptosis. This ability combined with the ability to include in the inert gel matrix only particularly selected biochemical factors can provide a culture system that can be used to greatly enhance the growth of CSCs or to greatly reduce the growth of CSCs. Moreover, the gels can be formed of biocompatible materials and as such can be utilized both in vivo and in vitro.

The disclosed matrices can be utilized in one embodiment to investigate the effect of matrix elastic modulus on the formation, growth, and maintenance of cancer cells (e.g., CSCs) by encapsulation of tumor cells in the hydrogel matrix in the absence of attached ligands that can interact with cell surface receptors. For example, and as further described herein, the disclosed matrices have been utilized to illustrate that the formation and maintenance of 4T1 mouse breast cancer cells and MCF7 human breast cancer cells can be modulated merely by the elastic modulus of the matrix.

In addition, the disclosed matrices can be utilized to selectively enrich or deplete a cell population in CSCs so as to better understand the development of tumors in the cell population, to examine the effects of potential treatment protocols on the cell population, and particularly on CSCs of a cell population, and so forth. For instance, the presence or absence within the gel of binding proteins or binding peptide fragments of entire proteins known to effect CSC growth and proliferation can be utilized to control the relative proportion of CSCs in an encapsulated cell population. This control can then be leveraged to better understand the effect of microenvironmental factors on the encapsulated cell population.

A cell population that can be examined can include a single cell type or multiple different cell types combined together, as desired. For instance, in one embodiment cancer stem cells can be encapsulated on the gel with no other cell types. In another embodiment, a cell population including cancer cells (e.g., breast cancer cells, lung cancer cells, etc.) and cancer stem cells can be encapsulated in a gel. For example, ex vivo tumor tissue including cancer cells and cancer stem cells in a proportion as found in vivo can be supported by the matrix. Of course, non-cancerous cells can also be encapsulated in or supported on a gel, for instance in conjunction with cancer cells and cancer stem cells. Other cells can include, without limitation, support cells or tumor stroma that can function as support for the growth of cancer cells. Support cells can include, without limitation, mesenchymal cells, endothelial cells, immune system cells, lymphatic cells, etc.

Through utilization of the disclosed gels it has been determined that the presence of a CD44 binding protein (e.g., RLVSYNGIIFFLK, SEQ ID NO.: 17) or a mutant thereof (e.g., VLFGFLKIYSRIN, SEQ ID NO.: 18) conjugated in the gel can inhibit breast tumorsphere formation in vitro and in vivo. In addition, tumorsphere formation in vitro can be enhanced by the presence of a fibronectin-derived heparin binding protein (FHBP) (e.g., WQPPRARI, SEQ ID NO.: 21) or a mutant thereof (e.g., RPQIPWAR, SEQ ID NO.: 22) while it can be abolished by the presence of an integrin binding RGD peptide (IBP), (e.g., GRGDS, SEQ ID NO.: 19) or a mutant thereof (e.g., GRDGS, SEQ ID NO.: 20).

The disclosed PEGDA hydrogel culture system can provide a useful tool to investigate the individual effect of factors such as these binding factors, optionally in conjunction with other biochemical factors in the microenvironment on cancer cell maintenance, and specifically on CSC maintenance, without interference of other factors. In turn, this can lead to the development of a 3D culture system with enriched population of CSCs for, e.g., drug testing.

As mentioned, the disclosed system can be developed with a predetermined elastic modulus in a well-defined narrow range. This can be very useful as the gel modulus can have a strong effect on tumorsphere formation and the effect can be bimodal. For instance, the stiffness of normal human breast tissue is lower than 4 kPa while that of cancerous breast tissue can be up to 40 kPa, and the disclosed matrices can be formed with an elastic modulus so as to reproduce the microenvironment of a biological system anywhere within this range. For example, the hydrogel matrix can be designed to have an intermediate elastic modulus of from 10 kilopascals (kPa) to 30 kPa, a low modulus of less than 10 kPa, for instance from 2.5 kPa to 7.5 kPa, or a high modulus of from 10 kPa to 70 kPa. In one embodiment, the hydrogel matrix can have a low modulus, but one that is higher than the modulus of normal tissue, which is generally less than 4 kPa. Thus, the hydrogel matrix can have a modulus of from 4 kPa to 6 kPa or a modulus of about 5.3 kPa in one embodiment. As described further herein, mouse 4T1 and human MCF7 cells encapsulated in a gel with 5.3 kPa modulus formed large tumorspheres at a high density of tumorspheres, and had high expression of breast CSC markers CD44 and ABCG2.

The stiffness of the gel matrix can be adjusted so as to replicate the ECM stiffness of the encapsulated cells when in vivo. The ECM stiffness is known to regulate proliferation and differentiation of many cell types. For instance, development of solid tumors is often accompanied by an increase in the stiffness of the local environment, and a high tissue density is a known risk factor for developing invasive breast carcinoma. Analysis of several cell lines in collagen matrices has revealed that matrix stiffness can dramatically affect the growth of certain cell lines but has little effect on others. For example, the growth of MDA-MB-231 cells, a highly malignant human breast cancer cell line, is significantly enhanced with increasing matrix stiffness while the growth of MCF-10a, a nonmalignant breast epithelial cell line, is relatively insensitive to matrix stiffness within a certain range. These results suggest that the response of cancer cells to matrix stiffness is not only dependent on the cancer but also on malignancy of the cancer. Furthermore, it has been reported that non-tumorigenic breast epithelial cells loose cell polarity and increase proliferation when cultured in matrices with 4.5 kPa stiffness. In addition, normal murine mammary gland or well-differentiated mammary epithelial cells cultured in high-density collagen matrices display an invasive phenotype. Mechanistic studies suggest that these mechanically induced transformations are associated with enhanced focal adhesion kinase (FAK) followed by FAK-dependent ERK and Rho activity. These pathways have been suggested as the circuit linking matrix stiffness to cytoskeleton.

The 3D system includes an inert synthetic polymer hydrogel that, in one embodiment, does not have any cell interaction ligands, thus providing a unique tool to study tumor microenvironment in vitro, as cell adhesion ligands are believed to mediate mechanosensing. Without wishing to be bound to any particular theory, the cell response to stiffness in the inert matrix is believed to be through the ECM secreted by the encapsulated cells. For example, human mesenchymal stem cells (hMSC) encapsulated in PEG hydrogels, in the absence of adhesive ligands, can secret their own ECM through which differentiation is directed by mechanotransduction. The disclosed matrices can be used to further elucidate such cellular activities. For instance, breast cancer CSCs are shown in the example section below to maintain their stemness and proliferate while the growth of non-CSCs was inhibited when encapsulated in the gel within a certain range of elastic moduli. Through variation and control of the elastic moduli of the gels in a predetermined fashion, further information regarding the interaction of encapsulated cells with the surrounding microenvironment can be elucidated.

In one embodiment, the synthetic polymer of the hydrogel can be PEG. This is not a requirement of the gel systems, however, and other synthetic inert and biocompatible polymers can be utilized in conjunction with or alternative to a PEG-based system. For instance, the inert synthetic gel can incorporate other polymers such as polyhydroxyethyl methacrylate (PHEMA), polyvinylpolypyrrolidone (PVP), and polyvinyl alcohol (PVA). The polymer can be any suitable molecular weight, with the preferred molecular weight depending upon the reactivity of the polymer as well as the targeted elastic modulus of the crosslinked hydrogel matrix. For instance, the polymer can be a low molecular weight polymer having a number average molecular weight of about 1,000 Da or less, a midrange molecular weight having a number average molecular weight of from about 1,000 Da to about 10,000 Da, or a high molecular weight, having a molecular weight of about 10,000 Da or greater. For instance, the polymer can be a difunctional polymer having a molecular weight of about 10,000 Da or less in one embodiment, or from about 1,000 Da to about 5,000 Da in some embodiments.

The stiffness of the system can be controlled through the crosslink density and/or the density of polymer chains of the hydrogel network. According to rubber elasticity theory, the gel elastic modulus is proportional to the density of elastically active chains and/or the crosslink density. Accordingly, the network crosslink density can be increased in one embodiment by increasing the concentration of the crosslinking agent in a precursor solution that includes a PEG macromer and the crosslinking agent, leading to the increase in matrix modulus. Likewise, by decreasing the concentration of the crosslinking agent in the precursor solution, the crosslink density and hence the elastic modulus of the formed gel can be decreased. Alternatively, the crosslink density and hence elastic modulus of the formed system can be controlled through variation in the molecular weight of the polymer included in a formation solution, with a higher molecular weight polymer leading to a lower elastic modulus and vice versa for a higher elastic modulus gel. Of course, polymer molecular weight can affect crosslink density of the hydrogel primarily in those embodiments in which the polymer includes a limited number of crosslinking sites, for instance in which the polymer is difunctional with crosslinking sites only at the termini of the polymer backbone chain.

The particular concentrations of the polymer and/or the crosslinking agent can vary to obtain a pre-determined elastic modulus, generally depending upon the reactive characteristics of the polymer. For example, in one embodiment, a precursor solution of a difunctional polymer and crosslinking agent (either prior to or following reaction of the polymer with the crosslinking agent) can have a polymer concentration of about 10% by weight of the solution or less to form a low elastic modulus hydrogel matrix (about 10 kPa or less), a polymer concentration of from about 10% by weight of the solution to about 20% by weight of the solution to form an intermediate elastic modulus hydrogel matrix (about 10 kPa to about 30 kPa), and a polymer concentration of about 20% by weight of the solution or greater to form a high elastic modulus hydrogel matrix (about 30 kPa or greater).

The crosslinking scheme utilized to form the hydrogel can vary depending upon the particular polymer used in the system. For instance, a crosslinking agent can be reacted with the polymer prior to gel formation or during gel formation, as desired. For example, in one embodiment a polymer (e.g., a PEG polymer) can first be functionalized to form a functional macromer (e.g., a PEG diacrylate) and the functional macromer can then be crosslinked to form the gel, for instance by use of an initiator, e.g., a photoinitiator, and subjection to suitable energy (e.g., a UV cure).

Alternatively, a crosslinking agent can be combined with a polymer that includes reactive functional groups at the time of gel formation, and the crosslinking agent can form links between and among the polymers to form the hydrogel network. The crosslinking agent can be a polyfunctional compound that can react with functionality of the polymer to form crosslinks within the hydrogel network. In general, the crosslinking agent can be a biocompatible non-polymeric compound, i.e., a molecular compound that includes two or more reactively functional terminal moieties linked by a bond or a non-polymeric (non-repeating) linking component. By way of example, the crosslinking agent can include but is not limited to diacrylates, di-epoxides, poly-functional epoxides, diisocyanates, polyisocyanates, polyhydric alcohols, water-soluble carbodiimides, diamines, diaminoalkanes, polyfunctional carboxylic acids, diacid halides, halo acrylate monomers, and so forth. For instance, when considering a PEG-based polymer, a non-polymeric acryloyl halide can be utilized as a crosslinking agent.

In some embodiments, an initiator is utilized to initiate crosslinking of the polymer. Initiators can include photo-initiators, thermal-initiators, or chemical initiators. For example, in one particular embodiment, a UV-initiator can be utilized. Chemical initiators can also be used, such as redox, peroxide, etc. In other embodiments, other radiation initiation processes, such as gamma rays, e-beam, X-ray, etc., can be utilized, which may not require the presence of an initiator.

For example, a non-limiting list of UV-initiators which may be used include IRGACURE® 184 (1-hydroxycyclohexyl phenyl ketone), IRGACURE® 2959 (4-(2-hydroxyethoxy)phenyl-(2-hydroxy-2-methylpropyl)ketone)), and DAROCURE® 1173 ($\alpha$-hydroxy-$\alpha$,$\alpha$-dimethylacetophenone), all commercially available from Ciba Specialty Chemicals (Terrytown, N.Y.).

Additional examples of suitable initiators (which may be photo-initiators or thermally activated initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, tutylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), actophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropylthioxanthone), benzyl 2-ethyl anthraquinone, methylbenzoyl formate, 2-hydroxy-2-methyl-1-phenylpropane-1-one, 2-hydroxy-4'-isopropyl-2-methyl propiophenone, .alpha.-hydroxy ketone, tetramethyl thiuram monosulfide, allyl diazonium salt, and combinations of camphorquinone and ethyl 4-(N,N-dimethylamino)benzoate.

When present, only one initiator is necessary, however, one or more second initiators may be utilized. The one or more second initiators can be photo or chemical initiators.

The amount of initiator can generally be supplied in standard amounts, for instance in the range of about 0.01 to about 5% by weight of the polymer solution The elastic modulus of a matrix can be predetermined to a very narrow range. For instance, the initial increase in tumorsphere size and cell number density with elastic modulus may be attributed to a deviation from normal tissue stiffness of only about 0.17 kPa. This small deviation can lead to matrix reorganization and change in the number and lifetime of integrin mediated interactions and related pathways. It has been reported that the sphere size of breast cancer cells encapsulated in collagen gels increased with an increase in elastic modulus from 0.17 to 1.20 kPa. In another study, it was shown that the proliferation and sphere size of hepatocellular carcinoma cells encapsulated in PEG-collagen gels increased with decreasing elastic modulus from 4 kPa (corresponding to the modulus of healthy liver) to 0.7 kPa. Accordingly, in one embodiment, the gel matrix can be formed with an elastic modulus that differs from the elastic modulus of a native ECM by about 3 kPa or less, for instance 3.3 kPa, or by 1 kPa or less, for instance from 0.17 kPa to 1.20 kPa from that of the native ECM.

A decrease in sphere size and cell number of the encapsulated cancer cells with increasing elastic modulus of the hydrogel system can be attributed to a decrease in mesh size and increase in retractive force of the gel network, leading to a negative contribution on the cell proliferation and sphere formation. The average pore size or the mesh size of the hydrogel can also affect diffusion of nutrients and oxygen and tumor cell motility. For example, HepG2 hepatocellular carcinoma cells form larger spheres when encapsulated in gels with larger pore sizes.

The mesh size of the gels disclosed herein can be, for example, from about 25 nanometers (nm) to about 95 nm, for instance from about 35 nm to about 70 nm. The mesh size can be calculated from the modulus and equilibrium swelling ratio of the gels using the Peppas and Barr-Howell equation, as is known in the art. For instance, as the functionalized PEG macromer concentration of a formation solution increases from 7.5% to 10, 15, 20, and 25%, the mesh size can decrease from 93±4 nm to 67±3, 53±3, 34±2, and 25±2 nm, respectively. Without wishing to be bound to any particular theory, the bimodal effect of gel modulus on tumorsphere formation may be due to the changes in the network mesh size that can affect cell-matrix interactions and nutrient diffusion as well due to changes in the gel modulus.

Unlike collagen and other biological gels, varying macromer concentration in the disclosed systems changes only the gel stiffness, not the ligand density in the matrix. Results detailed below of use of the disclosed system suggest that the stiffness of the tumor tissue alone can be sufficient to affect the fate of tumor cells. For instance, the biphasic behavior of CSC marker expression with time may be attributed to the fraction of CSCs in the gel, which can depend on the microenvironment, e.g., the stiffness of the surrounding environment and the mesh size of the surrounding environment.

In one embodiment, the gel can be conjugated with one or more binding peptides that can affect the proliferation of CSCs, so as to elucidate additional information about an encapsulated cell population and/or to selectively shut down/enhance the growth of CSCs in an encapsulated cell population. For example, a CD44 binding peptide (e.g., RLVSYNGIIFFLK (SEQ ID NO.: 17) or a mutant thereof (VLFGFLKIYSRIN (SEQ ID NO.: 18)) can be conjugated to the gel to inhibit proliferation of CSCs in the gel. A CD44 binding peptide (CD44BP) may be useful as CD44 expression is the most widely used marker for characterization and identification of breast CSCs. CD44 is a cell membrane glycoprotein involved in cell migration and adhesion. CD44 binds to many ECM ligands including hyaluronic acid (HA), osteopontin, fibronectin and collagen. It also binds to matrix metalloproteinases (MMPs) and growth factors to promote tumor invasion and growth. As such, CD44 utilizes many signaling pathways to regulate cell behavior, and its activity depends on conformational changes and post-translational modifications after ligand binding. CD44BP is a peptide derived from the D-domain of laminin α5 chain. It binds to CD44 and inhibits lung colonization of tumor cells in vivo but does not inhibit tumor cell proliferation when added to the culture medium.

CD44 has been used for CSC detection and targeting but the mechanism of its involvement in the maintenance of CSCs is not clear. Antibodies against CD44 are known to inhibit breast tumor growth and prevent cancer recurrence. Anti-CD44 antibodies have been found to induce the differentiation of acute myeloid leukemia (AML) stem cells. In addition, a CD44 exon v6-specific antibody has been found to block the metastasis of rat pancreatic cancer cells. Therefore, utilization of CD44 binding peptide to regulate CSC population in the disclosed systems can provide critical information on the behavior of breast CSCs and/or on the behavior of other cancer cells following depletion of the CSCs from a combined cell population.

Of course, the effect of other biochemical factors on cancer cells and in particular on CSCs can be examined in conjunction with the disclosed matrices. For instance, binding peptides including an integrin binding RGD peptide (IBP) (e.g., GRGDS (SEQ ID NO.: 19) or a mutant thereof GRDGS (SEQ ID NO.: 20)) or a fibronectin-derived heparin-binding peptide (FHBP) (WQPPRARI (SEQ ID NO.: 21) or a mutant thereof RPQIPWAR (SEQ ID NO.: 22)) can be conjugated to the gel to either enhance or deplete the CSC population in the gel and investigate in vitro the effect of a biochemical factor on encapsulated cells. These two peptides may be useful as fibronectin is one of the major components of ECM that mediates cell adhesion, and integrins are the major receptors on the cell surface that sense the environmental cues. In the specific examples described below, the results show that conjugation of FHBP to the gel matrix enhanced tumorsphere formation by encapsulated 4T1 breast cancer cells while CD44BP and IBP abolished sphere formation in vitro.

The RGD integrin binding peptide is present in many ECM components and can be beneficially utilized to examine a cancer cell population, but there are other binding motifs in the ECM that can alternatively be utilized. For example, fibronectin has RGD-independent heparin-binding domain in the C-terminus and binds to heparin sulfate proteoglycans on the surface of tumor cells.

Moreover, biochemical factors that can be investigated by use of the system are not limited to binding proteins. The natural cell microenvironment is composed of many cellular and non-cellular components such as cell binding proteins, growth factors, and nutrients, any of which can be incorporated in a matrix as disclosed herein. Moreover, variants of natural biochemical factors can be incorporated in a matrix including, without limitation, fragments, mutants, homologues, orthologues, analogues, etc. of naturally occurring proteins can be incorporated in a matrix. In addition, the biochemical factors to be examined can be incorporated in the hydrogel matrix or can be included in a cell culture medium in which the hydrogel and encapsulated cell population can be incubated.

In one embodiment, the biochemical factor can include a cancer drug. For instance, a hydrogel matrix that encapsulates a cell population can be incubated in a cell culture medium that includes a cancer drug. In addition, the hydrogel matrix can include a conjugated peptide that can affect the proliferation of cancer stem cells included in the cell population (e.g., either enhance the proliferation of the CSCs or deplete the population of the CSCs). Through study of the system, the usefulness of the biochemical factor as a cancer drug can be determined.

Any cancer drug and any type of cell population are encompassed herein. As utilized herein, the term "cancer drug" generally refers to any agent useful to combat cancer. A non-limiting list of cancer drugs that can investigated by use of the disclosed matrices can be found in, for example, U.S. Pat. No. 5,037,883, which is incorporated herein by reference. U.S. Pat. Nos. 6,348,209, 6,346,349, and 6,342,221 also describe agents related to cancer drugs, all of which are incorporated herein by reference.

Classes of cancer drugs encompassed herein include, but are not limited to, chemotherapeutic agents, cytotoxins, antimetabolites, alkylating agents, protein kinase inhibitors, anthracyclines, antibiotics, antimitotic agents (e.g. antitubulin agents), corticosteroids, radiopharmaceuticals, and proteins (e.g. cytokines, enzymes, or interferons). Cancer drugs can include, for example, small molecule organic compounds, macromolecules, metal containing compounds, and compounds or chelates that include radionuclides. In example embodiments, the cancer drug can be a small molecule organic compound. Specific examples include, but are not limited to docetaxel, gemcitabine, imatinib (Gleevece®), 5-fluorouracil, 9-aminocamptothecin, amine-modified geldanamycin, doxorubicin, paclitaxel (Taxon, cis-platin, procarbazine, hydroxyurea, meso e-chlorin, Gd(+3) compounds, asparaginase, and radionuclides (e.g. 1-131, Y-90, In-111, and Tc-99m). There are many cancer drugs known in the art and many continue to be developed. In some embodiments, two or more cancer drugs can be examined simultaneously.

Due to the complex biochemical composition of the natural microenvironment, it is difficult to study the role of individual factors on cell behavior with in vitro models. By use of the disclosed inert system with controlled elastic modulus, any biochemical factor or combination thereof can be investigated to determine the effect on the growth, proliferation and maintenance of cancer cells (for instance on the stemness of breast CSCs) without the interference of other factors. Further, the ability of the system to selectively enrich CSCs in an encapsulated cell population can be of great benefit for drug testing.

Biochemical factors can be conjugated to the hydrogel matrix according to any suitable fashion that can maintain the activity of the factor. For instance, in one embodiment the biochemical factors can be covalently coupled to the macromer of the hydrogel matrix via reactive functionalization of the biochemical factor. Alternatively, a biochemical factor can be non-covalently coupled in the matrix, for instance by charge-charge interaction or through encapsulation. For instance, a relatively large biochemical factor, e.g., a complete protein, can be encapsulated in the matrix at the time of matrix formation and contained within the matrix as the mesh size of the matrix is smaller than the size of the biochemical factor.

The presently disclosed subject matter may be better understood with reference to the Examples set forth below.

Example 1

Materials

Polyethylene glycol (PEG, nominal molecular weights 4.6 kDa), dichloromethane (DCM), N,N-dimethylformamide (DMF), diethyl ether, and hexane were purchased from Acros (Fairfield, Ohio). Calcium hydride, triethylamine (TEA), paraformaldehyde, 4,6-diamidino-2-phenylindole (DAPI), insulin, penicillin, and streptomycin were purchased from Sigma-Aldrich (St. Louis, Mo.). Basic fibroblast growth factor (bFGF) and epidermal growth factor (EGF) were purchased from Lonza (Allendale, N.J.). Bovine serum albumin (BSA) was obtained from Jackson ImmunoResearch (West Grove, Pa.). Dulbecco's phosphate-buffer saline (PBS), trypsin-EDTA, RPMI-160 cell culture medium, DMEM F12 medium, fetal bovine serum (FBS), Alexa Fluor® 594 Phalloidin, and Quant-it PicoGreen dsDNA reagent kit were purchased from Invitrogen (Carlsbad, Calif.). Horse serum was purchased from PAA Laboratories (Etobicoke, Ontario) and DMEM-F12 was from Mediatech (Manassas, Va.). Spectro/Por dialysis tube (molecular weight cutoff 3.5 kDa) was purchased from Spectrum Laboratories (Rancho Dominguez, Calif.). DCM was purified by distillation over calcium hydride. All other solvents were reagent grade and were used as received without further purification. Anti-CD44 antibody (HCAM, DF1485) was from Santa Cruz Biotechnology (Santa Cruz, Calif.). Monoclonal Anti-BrdU antibody proliferation marker (produced in mouse) was obtained from Sigma-Aldrich. Fluorescent conjugated secondary antibodies were obtained from Invitrogen. 4T1 mouse breast carcinoma and MCF7 human breast adenocarcinoma cell lines were received from the Scripps Research Institute (La Jolla, Calif.) and American Type Culture Collection (ATCC, Manassas, Va.), respectively. The Live/Dead calcein AM (cAM) and ethidium homodimer-1 (EthD) cell viability/cytotoxicity kit was purchased from Molecular Probes (Life Technologies, Grand Island, N.Y.).

Macromer Synthesis and Characterization

The PEG macromer was functionalized with acrylate groups to produce polyethylene glycol diacrylate (PEGDA) by the reaction of acryloyl chloride with hydroxyl end-groups of PEG, as shown in FIG. 1A. TEA was used as the reaction catalyst. Prior to the reaction, PEG was dried by azeotropic distillation from toluene to remove residual moisture. The polymer was dissolved in dried DCM in a reaction flask, the flask was immersed in an ice bath to cool the polymer solution and limit the temperature rise from the exothermic reaction. In a typical reaction 5.6 mL acryloyl chloride and 9.7 mL TEA, each dissolved in DCM, were added drop-wise to the reaction with stirring. The reaction was allowed to proceed for 12 h under nitrogen flow. After completion of the reaction, the solvent was removed by rotary evaporation and the residue was dissolved in anhydrous ethyl acetate to precipitate the by-product triethylamine hydrochloride salt. Next, ethyl acetate was removed by vacuum distillation; the macromer was re-dissolved in DCM and precipitated twice in ice-cold ethyl ether. The macromer was dissolved in dimethylsulfoxide (DMSO) and dialyzed against distilled deionized (DI) water to remove the by-products. The PEGDA product was freeze-dried and stored at −20° C. The chemical structure of the functionalized macromer was characterized by a Varian Mercury-300 1H-NMR (Varian, Palo Alto, Calif.) at ambient conditions with a resolution of 0.17 Hz. The sample was dissolved in deuterated chloroform at a concentration of 5 mg/mL and 1% v/v TMS was used as the internal standard.

Hydrogel Synthesis and Measurement of Gel Modulus

The PEGDA macromers were crosslinked in aqueous solution by UV initiated radical polymerization with 4-(2-hydroxyethoxy)phenyl-(2-hydroxy-2-propyl) ketone (Irgacure 2959; CIBA, Tarrytown, N.Y.) photoinitiator. 5 mg of initiator was dissolved in 1 mL PBS at 50° C. The macromer was dissolved in PBS by vortexing and heating to 50° C. To prepare 7.5, 10, 15, 20 and 25% PEGDA hydrogel precursor solutions, 22.5, 30, 45, 60 and 75 mg of PEGDA macromer was mixed with 278, 270, 255, 240 and 225 μL of the initiator solution, respectively, by vortexing for 5 min. For cell loading, $1.4 \times 10^5$/mL 4T1 cells suspended in PBS were added to the macromer solution and mixed gently with a glass rod. The hydrogel precursor solutions were degassed and transferred to a PTFE mold (5 cm×3 cm×750 μm), covered with a transparent glass plate, fastened with clips, and UV irradiated with a BLAK-RAY 100-W mercury long wavelength (365 nm) UV lamp (Model B100-AP; UVP, Upland, Calif.) for 10 min. Disc shape samples were cut from the gel using an 8 mm cork borer and swollen in PBS for 24 h at 37° C. To measure the gel's elastic modulus, samples were loaded on the Peltier plate of the rheometer (TA Instruments, New Castle, Del.) and subjected to a uniaxial compressive force at a displacement rate of 7.5 μm/s. The slope of the linear fit to the stress-strain curve for 5-10% strain was taken as the elastic modulus (E) of the gels.

Cancer Stem Cell Culture and Characterization

4T1 and MCF7 tumor cells were cultured in RMPI-1640 medium with 10% FBS under 5% $CO_2$ at 37° C. Cells were trypsinized after reaching 70% confluency. PEGDA macromer was dissolved in PBS and sterilized by filtration with a 0.2 μm filter. Next, $1.4 \times 10^5$/mL 4T1 or MCF7 cells suspended in PBS were added to the macromer solution with final PEGDA concentrations ranging 5-25 wt % and mixed gently with a pre-sterilized glass rod. The cell-suspended hydrogel precursor solution was crosslinked with UV for 10 min. After crosslinking, the gel was cut into disks and incubated in stem cell culture medium in ultra-low attachment tissue culture plates under 5% $CO_2$. The stem cell medium consisted of DMEM-F12 supplemented with 0.4% bovine serum albumin (BSA), 5 μg/mL insulin, 40 ng/mL basic fibroblast growth factor (bFGF), 20 ng/mL EGF, 5% horse serum, 100 U/mL penicillin, and 100 μg/mL streptomycin.

For growing tumorspheres in suspension, trypsinized 4T1 cells were cultured on ultra-low attachment tissue culture plates with stem cell culture medium under 5% $CO_2$ at 37° C. as described previously. The gold standard for characterization of CSC tumorspheres for stemness is by the ability to form tumor. To test for tumor formation, a stable 4T1 cell line that expressed luciferase (4T1-Luc) was established as known. Luciferase expression vector pGL4.50[Luc2/CMV/Hygro] (Promega, Madison, Wis.) was transfected into 4T1 cells by Lipofectamine 2000 (Invitrogen), according to the manufacturer's instructions, to generate a cell line expressing luciferase as a reporter. After 24 h, cells were trypsinized and cultured in RPMI-1640 medium with 400 μg/mL of hygromycin for 3 weeks to generate 4T1-Luc cells. 4T1-Luc cells were cultured on adhesion plates with regular RPMI-1640 culture medium or on ultra-low attachment plates with stem cell culture medium as describe above. After one week, cells were trypsinized and counted. Different number of cells (5000 and 50,000 cells from adhesion plates or 500, 1,000 and 5,000 tumorsphere cells from ultra-low attachment plates) was injected subcutaneously in syngeneic Balb/C mice (6 mice/group). One week after inoculation, 100 μL of D-Luciferin (30 mg/mL, Caliper, Hopkinton, Mass.) was injected subcutaneously and mice were imaged 10 min after Luciferin injection by Caliper's IVIS Spectrum imaging system (Caliper Life Sciences, Hopkinton, Mass.).

Cell Imaging and Determination of Cell Number

To determine cell viability, gels were stained with cAM/EthD live/dead dyes 2 days after encapsulation to image live and dead cells, respectively. Stained samples were imaged with an inverted fluorescent microscope (Nikon Eclipse Ti-ε, Nikon, Melville, N.Y.). Cell viability was quantified by dividing the image into smaller squares and counting the number of live and dead cells. At each time point, the gel samples were removed from the culture media and stained for imaging. Samples were rinsed twice with PBS and fixed with 4% paraformaldehyde for 3 h. After fixation, cells were permeabilized using PBS containing 0.1% Triton X-100 for 5 min. After rinsing, cells were incubated with Alexa 488 phalloidin (1:200 dilution) and DAPI (1:5000 dilution) to stain actin filaments of the cell cytoskeleton and cell nuclei, respectively. Stained samples were imaged with a Nikon Eclipse Ti-ε inverted fluorescent microscope. For visualization of cell uniformity, a confocal fluorescent microscope (Zeiss LSM-510 META Axiovert, Carl Zeiss, Germany) was used to obtain 2D images (90 μm thick layers) of the stained gels in the direction of thickness. For determination of cell number, the gel samples were homogenized, cells were lysed, and aliquots were used to measure the double stranded DNA (dsDNA) content using a Quant-it PicoGreen assay. Briefly, an aliquot (100 μL) of the working solution was added to 100 μL of the cell lysate and incubated for 4 min at ambient conditions. The fluorescence of the solution was measured with a plate reader (Synergy HT, Bio-Tek, Winooski, Vt.) at emission and excitation wavelength of 485 and 528m nm, respectively. Measured fluorescent intensities were correlated to cell numbers using a calibration curve constructed with 4T1 or MCF7 cells of known concentration ranging from zero to 105 cells/m L.

BrdU Retention Assay and Immunofluorescent Imaging

BrdU label-retention was used to identify mammary cancer stem cells. Nonconfluent 4T1 cells were incubated with 10 μM of BrdU for 10 days to label the DNA by incorporating BrdU into replicating DNA in place of thymidine. Next, the BrdU labeled cells were encapsulated in the gel and incubated in stem cell culture medium to form tumorspheres as described above. At each time point, the retention of BrdU in the encapsulated cells was imaged by immunofluorescent staining with Anti-BrdU antibodies. At each time point, tumorspheres encapsulated in the gel samples were processed and stained for immunofluorescent imaging of BrdU-labeled cells or CD44 marker. Gel Samples were fixed and permeabilized for 3 h at 4° C. in PBS containing 4% paraformaldehyde and 1% Triton X-100, followed by rinsing with PBS (3×10 min). Tumor spheroids were then dehydrated in an ascending series of methanol at 4° C. in PBS (25%, 50%, 75%, 95%, 30 min each and 100% for 5 h) and rehydrated in the same descending series and washed in PBS (3×10 min). Next, samples were blocked with PBS containing 0.1% Triton X-100 (PBST) and 3% BSA overnight at 4° C. and washed with PBS (2×15 min). Then, samples were incubated with primary antibodies (anti-CD44 antibody or anti-BrdU antibody) diluted in PBST on a gently rocking rotator at 4° C. overnight followed by rinsing with PBST (4×30 min). Samples were then incubated with Alexa Fluor conjugated secondary antibodies for 2 h and rinsed with PBST (4×10 min). The cell nuclei were counterstained with DAPI (1:5000 dilution in PBS) and imaged with a Nikon Eclipse Ti-ε inverted fluorescent microscope.

mRNA Analysis

Total cellular RNA of the gel samples was isolated using TRIzol (Invitrogen). 250 ng of the extracted purified RNA was reverse transcribed to cDNA by SuperScript II Reverse Transcriptase (Invitrogen) with the random primers. The obtained cDNA was subjected to real time quantitative polymerase chain reaction (RT-qPCR) amplification with appropriate gene specific primers. RT-qPCR was performed to analyze the differential expression of CSC markers CD44 (4T1 and MCF7), CD24 (4T1), ABCG2 (4T1 and MCF7), and SCA1 (4T1) genes with SYBR green RealMasterMix (Eppendorf, Hamburg, Germany) using Bio-Rad iCycler PCR system (Bio-Rad, Hercules, Calif.). The expression level of GAPDH gene was used as an internal control. The primers for real time PCR were designed by Primer 3 software. The following forward and reverse primers synthesized by Integrated DNA technologies (Coralville, Iowa) were used: mouse GAPDH: forward 5'-CAT GGC CTT CCG TGT TCC TA-3' (SEQ ID NO: 1) and reverse 5'-CCT GCT TCA CCA CCT TCT TGA-3' (SEQ ID NO: 2); mouse CD44: forward 5'-GAA TGT AAC CTG CCG CTA CG-3' (SEQ ID NO: 3) and reverse 5'-GGA GGT GTT GGA CGT GAC-3' (SEQ ID NO: 4); mouse CD24: forward 5'-CTT CTG GCA CTG CTC CTA CC-3' (SEQ ID NO: 5) and reverse 5'-GAG AGA GAG CCA GGA GAC CA-3' (SEQ ID NO: 6); mouse ABCG2: forward 5'-AGC AGC AAG GAA AGA TCC AA-3' (SEQ ID NO: 7) and reverse 5'-GGA ATA CCG AGG CTG ATG AA-3' (SEQ ID NO: 8); mouse SCA1: forward 5'-TGG ACA CTT CTC ACA CTA-3' (SEQ ID NO: 9) and reverse 5'-CAG AGC AAG AGG GTC TGC AGG AG-3' (SEQ ID NO: 10); human GAPDH forward 5'-GAG TCA ACG GAT TTG GTC GT-3' (SEQ ID NO: 11) and reverse 5'-TTG ATT TTG GAG GGA TCT CG-3' (SEQ ID NO: 12); human CD44 forward 5'-GGC TTT CAA TAG CAC CTT GC-3' (SEQ ID NO: 13) and reverse 5'-ACA CCC CTG TGT TGT TTG CT-3' (SEQ ID NO: 14); human ABCG2 forward 5'-CAC CTT ATT GGC CTC AGG AA-3' (SEQ ID NO: 15) and reverse 5'-CCT GCT TGG AAG GCT CTA TG-3' (SEQ ID NO: 16). The relative gene expression levels were quantified by the $2^{-ddCT}$ method as described. The relative gene expressions were expressed as fold difference compared with that at time zero.

Statistical Analysis

Data are expressed as means±standard deviation. All experiments were done in triplicate. Significant differences between groups were evaluated using a two-way ANOVA with replication test followed by a two-tailed Student's t-test. A value of $p<0.05$ was considered statistically significant.

Macromer Characterization and Hydrogel Modulus

The reaction scheme for acrylation of PEG macromer and the NMR spectrum of PEGDA are shown in FIG. 1A and FIG. 1B, respectively. The chemical shifts with peak positions at 3.6 and 4.3 ppm were attributed to the methylene hydrogens (=CH₂) of PEG attached to ether (—CH₂—O—CH₂) and ester (—CH₂—OOC—) groups, respectively. The shifts with peak positions from 5.85 to 6.55 ppm (see inset in FIG. 1B) were attributed to the vinyl hydrogens (—CH=CH₂-) of the acrylate group at the end of each macromer arm as follows: Peak positions in the 5.82-5.87 ppm range were associated with the trans proton of unsubstituted carbon of the Ac; those in the 6.10-6.20 ppm range corresponded to the protons bonded to monosubstituted carbon of the Ac; and those in the 6.40-6.46 ppm range were associated with the proton of unsubstituted carbon of the acrylate group. The number of acrylate groups per macromer was determined from the ratio of NMR shifts between 5.85 and 6.55 ppm (acrylate hydrogens) to those at 3.6 and 4.2 ppm (PEG hydrogens). 46, 47 Based on NMR results, the average degree of acrylation was 89% and there was on average 1.8±0.1 acrylates in the PEGDA macromer. Disk shape hydrogels with 8 mm diameter and 750 μm thickness were fabricated for determination of elastic modulus and cell encapsulation. The effect of macromer concentration and incubation time on the elastic modulus of PEGDA hydrogel, loaded with 4T1 cells, is shown in FIG. 2. Macromer concentration in the precursor solution affected the elastic modulus of the hydrogel. The elastic modulus increased from 2.5±0.7 kPa to 5.3±1.4, 26.1±6.9, 47.5±11.6 and 68.6±9.3 kPa as the macromer concentration was increased from 5% to 10, 15, 20 and 25%, respectively. The elastic modulus of the gels, with encapsulated 4T1 cells, did not change significantly during 14 days of incubation in the cell culture medium, as shown in FIG. 2.

Tumorsphere Characterization

Tumorsphere formation on ultra-low attachment plates is a commonly used method to enrich CSCs in vitro, while the gold standard for characterization of CSC tumorspheres is by the ability to form tumor in vivo. 4T1-Luc cells were cultured on regular adhesion plates or ultra-low attachment plates. After one week, cells in monolayers (adhesion plates) and in spheres (ultra-low attachment plates) were collected and subcutaneously inoculated in syngeneic Balb/c mice. Tumor formation in mice was determined by imaging the expression of luciferase one week after inoculation. FIG. 3 compares tumor formation by cells on adhesion plates (Panel A) and cells from tumorspheres on ultra-low attachment plates (Panel B). The left and right images in Panel A are for 5000 and 50,000 4T1-Luc cells on adhesion plates. The left, center, and right images in Panel B are for 500, 1000, and 5000 4T1-Luc cells from tumorspheres on ultra-low attachment plates. According to the images in FIG. 3, 1000 tumorsphere cells were sufficient to form a tumor in vivo while it required 50,000 regular tumor cells to form a tumor. These results demonstrate that tumorspheres formed by 4T1 cells in vitro had enriched CSC subpopulation.

Tumorsphere Formation in Hydrogel

Figure 4:
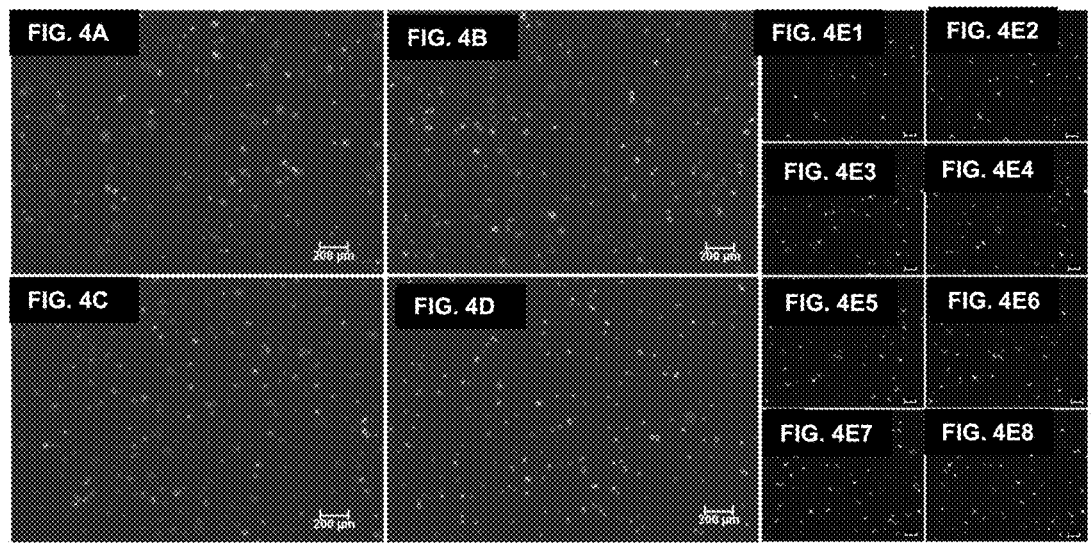
FIG. 4 presents live and dead images of 4T1 cells 2 days after encapsulation in PEGDA hydrogels with moduli of 2.5 kPa (FIG. 4A), 5.3 kPa (FIG. 4B), 26.1 kPa (FIG. 4C) and 47.5 kPa (FIG. 4D). The scale bars in images of FIG. 4A, FIG. 4B, FIG. 4C, and FIG. 4D are 200 µm. Based on image analysis, the percent viable cells for the 2.5, 5.3, 26.1, 47.5 and 68.6 kPa gels was 94±4, 91±3, 92±3, 90±4, and 89±4, respectively.

4T1 tumor cells were encapsulated in PEGDA hydrogels with elastic moduli ranging from 2 to 70 kPa and cultured in stem cell medium for 2 weeks. Images of live and dead cells 2 days after encapsulation in PEGDA gels with moduli of 2.5, 5.3, 26.1 and 47.5 kPa are shown in FIG. 4A, FIG. 4B, FIG. 4C, and FIG. 4D, respectively. Based on image analysis, the percent viable cells for 2.5, 5.3, 26.1, 47.5 and 68.6 kPa gels were 94±4, 91±3, 92±3, 90±4, and 89±4, respectively. These results show that the gel modulus did not have a significant effect on viability of 4T1 cells after encapsulation. To determine cell uniformity and viability, a confocal microscope was used to image cells in the direction of thickness and the results are shown in images FIG. 4E1 through FIG. 4E8 4. Images in FIG. 4E show uniform cell seeding and cell viability within the gel in the thickness direction.

Figure 5:
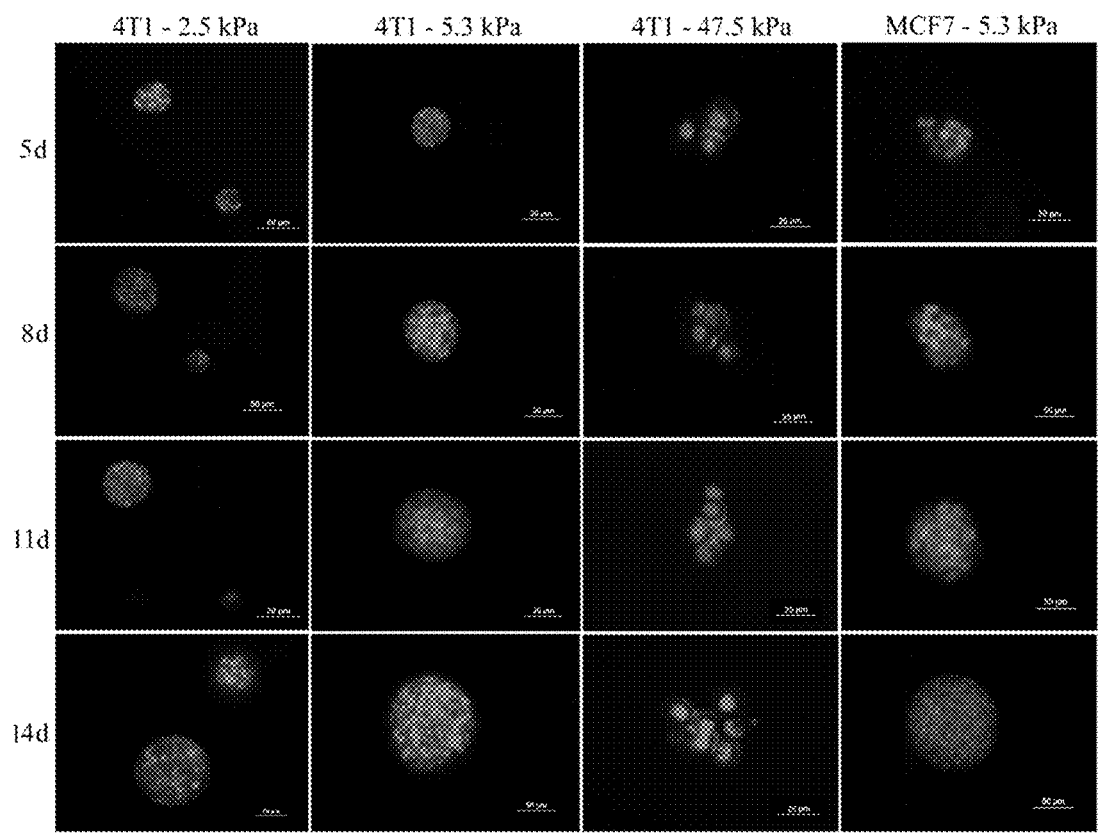
Figure 6:
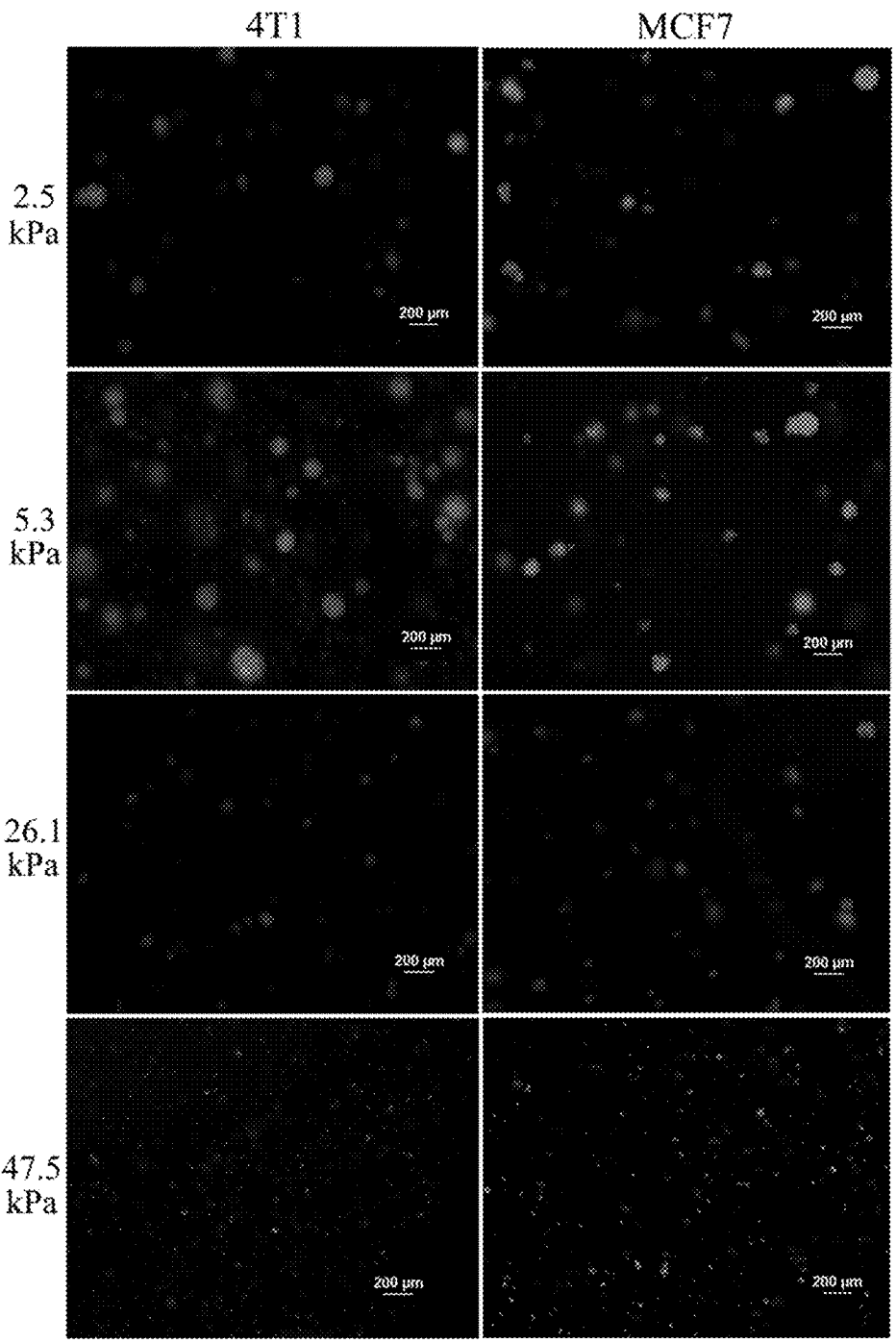

Fluorescent images in FIG. 5 show the extent of cell aggregation and spheroid formation with incubation time for 4T1 gels with modulus of 2.5 kPa (FIG. 5, $1^{st}$ column), 5.3 kPa (FIG. 5, $2^{nd}$ column), 47.5 kPa (FIG. 5, $3^{rd}$ column), and MCF7 gel with 5.3 kPa (FIG. 5, $4^{th}$ column). Rows 1, 2, 3, and 4 in FIG. 5 correspond to incubation times of 5, 8, 11, and 14 days, respectively. Spheroid formation was observed in soft gels with moduli of 2.5 and 5.3 kPa as early as day 5 (1st, $2^{nd}$, and 4th columns in FIG. 5) while cells in the more stiff gels with modulus of 47.5 kPa and higher remained as single cells or small cell aggregates (<25 μm). MCF7 human breast cancer cells also formed spheres when encapsulated in the gel with modulus of 5.3 kPa (FIG. 5, $4^{th}$ column). At any time point, size of the tumorspheres in the 5.3 kPa gel was higher than that of 2.5 kPa gel. Lower magnification images in FIG. 6 show the number density of 4T1 and MCF7 tumorspheres in PEGDA gels with elastic moduli of 2.5 kPa, 5.3 kPa, 26.1 kPa, and 47.5 kPa after 8 days of incubation. According to FIG. 6, the tumorsphere size and number density initially increased with increasing matrix modulus from 2.5 to 5.3 kPa and then decreased when modulus was increased to 26.1 and 47.5 kPa. Tumorspheres with diameter >100 μm was observed only in the gels with modulus of 2.5 and 5.3 kPa but the fraction of large tumorspheres (>100 μm) was significantly higher in the 5.3 kPa gel. It should be noted that the size of MCF7 spheroids in the gels was less than that of 4T1.

Tumorsphere Size and Number Density

Figure 7:
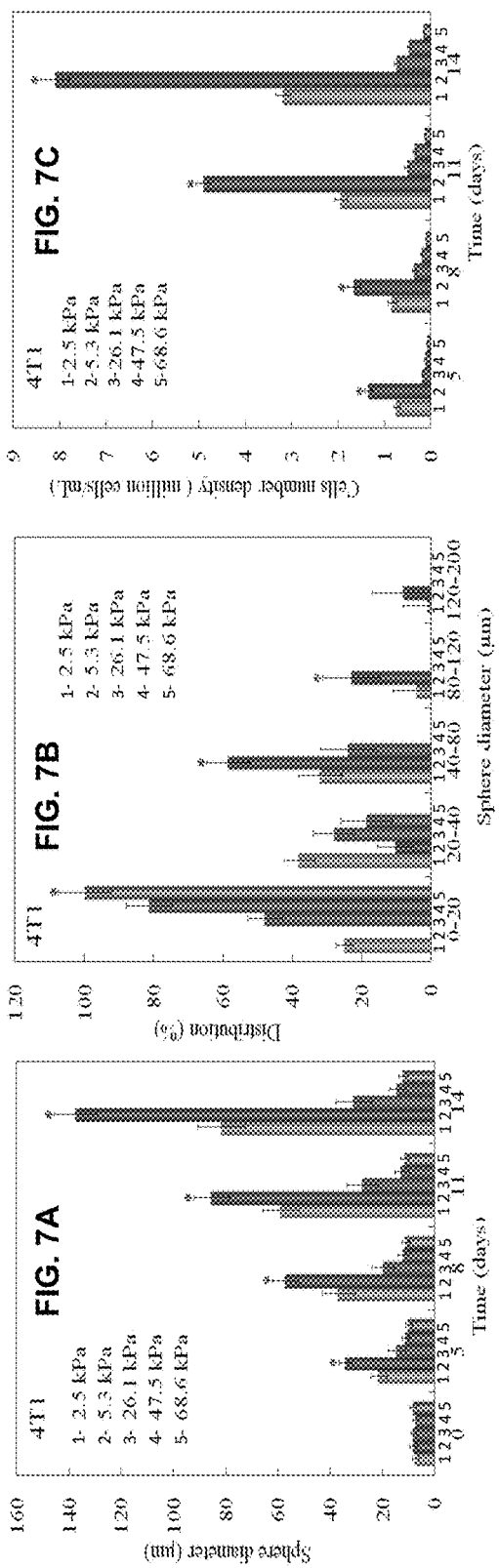
Figure 7:
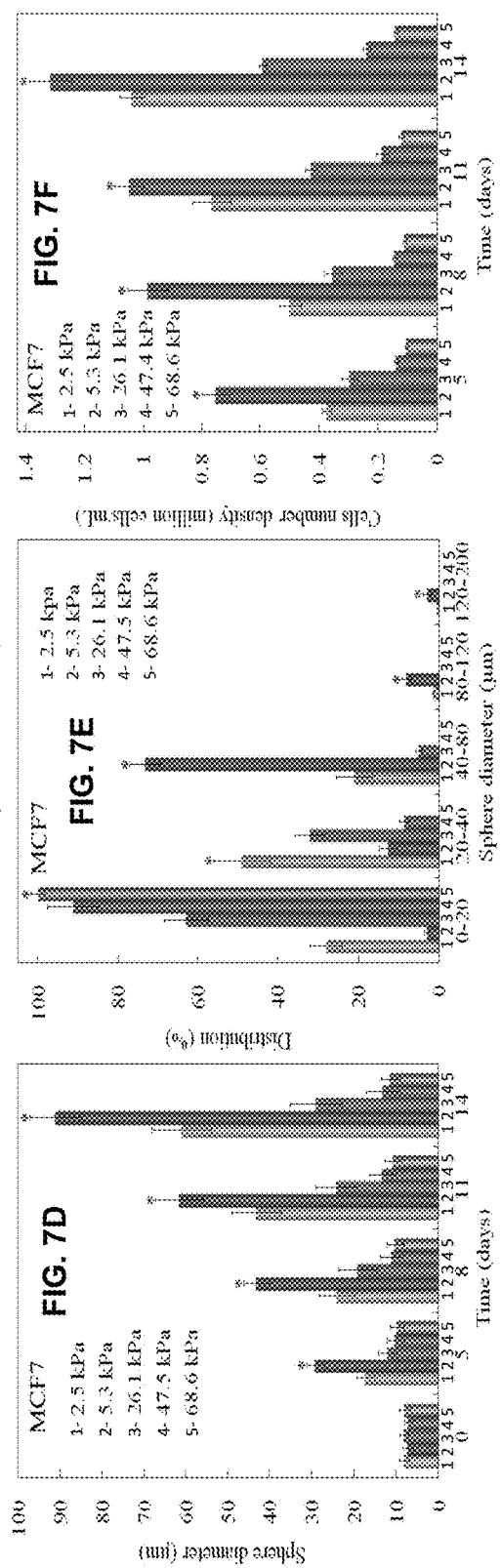

The effect of hydrogel modulus on average tumorsphere diameter and size distribution with incubation time is shown in FIG. 7A and FIG. 7B for 4T1 cells and FIG. 7D and FIG. 7E for MCF7 cells, respectively. The average 4T1 tumorsphere diameter increased from 10 μm at day zero to 80, 140, 30, 15, and 10 μm after 14 days as the gel modulus increased from 2.5 kPa to 5.3, 26.1, 47.5, and 68.6 kPa, respectively, while tumorsphere diameter for MCF7 cells increased from 8 μm at day zero to 60, 90, 29, 13, and 11 μm after 14 days. For 4T1 cells in the softest gel (2.5 kPa modulus), 25% of the cell aggregates at day 8 had <20 μm size (single cell fraction) while there was no single cell subpopulation in the gel with 5.3 kPa modulus. For MCF7 cells after 8 days, 28% and 3% of the cell aggregates had <20 μm size in 2.5 and 5.3 kPa gels, respectively. Furthermore, for the gel with 5.3 kPa modulus, 23% and 8% of 4T1 tumorspheres and 8% and 3% of MCF7 tumorspheres had size in the range of 80-120 and 120-200 μm, respectively. The fraction of tumorspheres with 0-20 μm diameter (single cell fraction) increased with increasing gel modulus for 4T1 and MCF7 cells and all of the cells in the highest modulus gel (68.6 kPa) remained as single cells.

The number density of viable 4T1 and MCF7 cells in PEGDA gels with different moduli is shown in FIG. 7C and FIG. 7F, respectively. The cell count increased with time for all groups but the gels with moduli of 2.5 and 5.3 kPa had the highest cell count at all time points. At each time point, the change in cell count with gel modulus was bimodal, that is the cell count initially increased for moduli of 2.5 and 5.3 kPa and then decreased for gels with moduli >26 kPa. At day 14, the 5.3 kPa gel had 3 fold higher 4T1 cell and 1.3 fold higher MCF7 cell than the 2.5 kPa gel; the 5.3 kPa gel had 10 fold higher 4T1 and MCF7 cells than those gels with >26 kPa modulus. In general, the gel modulus has similar effects on 4T1 and MCF7 cells. These results demonstrate that the gel with modulus of 5.3 kPa had the highest potential for tumorsphere formation in the absence of ligand-receptor interactions.

Tumorsphere Marker Expression

Figure 8:
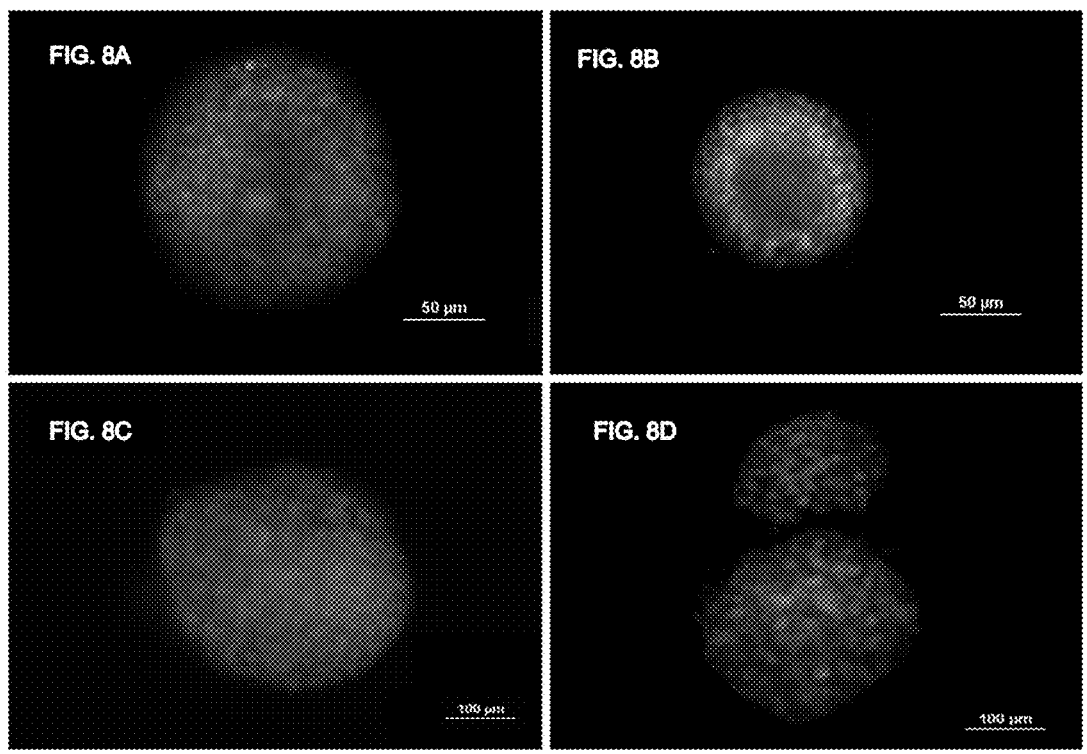

One of the unique properties of CSCs is asymmetrical division and retention of DNA labeling. Based on this feature, BrdU retention is a commonly used method to characterize CSCs. 4T1 cells were labeled with BrdU before encapsulation in the PEGDA gel with 5.3 kPa modulus and the intensity of BrdU staining was compared with those cells cultured on ultra-low attachment plates. FIG. 8 compares BrdU staining of 4T1 cells in suspension culture on ultra-low attachment plates (FIG. 8A and FIG. 8C) with those encapsulated in PEGDA hydrogels (FIG. 8B and FIG. 8D). FIG. 8A and FIG. 8B were obtained after 8 days of culture while FIG. 8C and FIG. 8D were obtained after 14 days. After 8 and 14 days, cells encapsulated in the gel displayed higher level of BrdU retention than those in suspension cultures, suggesting that the encapsulated tumorspheres had higher fraction of CSCs.

Figure 9:
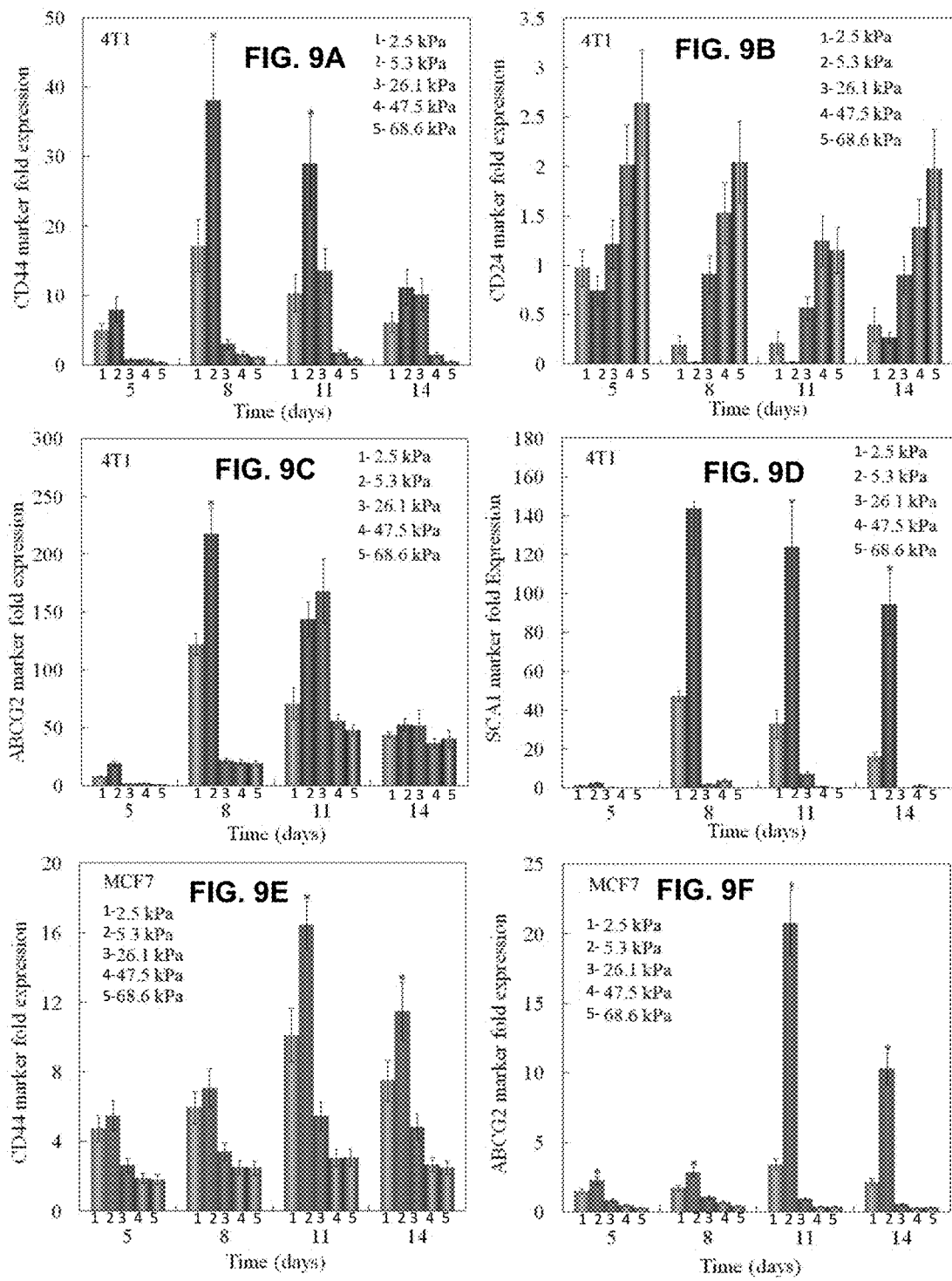
FIG. 9 presents the effect of gel elastic modulus on the relative mRNA expression levels of CD44 (FIG. 9A), CD24 (FIG. 9B), ABCG2 (FIG. 9C), Sca1 (FIG. 9D) markers of 4T1 cells, and CD44 (FIG. 9E), ABCG2 (FIG. 9F) markers of MCF7 cells encapsulated in PEGDA hydrogels with incubation time. The mRNA expression levels of the markers for 4T1/MCF7 cells before encapsulation were used as reference (set equal to one). The star indicates statistically significant difference between the test group and all other groups at the same time point. Error bars correspond to means±1 SD for n=3.

The expressions of breast CSC markers for tumorspheres grown in PEGDA gels with different moduli are shown in FIG. 9. FIG. 9A through FIG. 9D show the expression of CD44, CD24, ABCG2, and SCA1 for 4T1 cells and FIG. 9E and FIG. 9F show the expression of CD44 and ABCG2 for MCF7 cells. ABCG2 of ABC transporter proteins is responsible for CSC drug resistant and SCA1 (stem cell antigen-1) is a cell surface protein known to be associated with breast CSCs. 48-50 CD44 and ABCG2 are well-studied markers in both mouse and human breast cancer stem cells. Although CD24– is also a marker often used as a breast CSC marker, recent studies indicate that both CD44+/CD24– and CD44+/CD24+ cells display CSC phenotypes in MCF7 cells. SCA1 is a murine stem cell marker and it is unclear whether SCA1 is a CSC marker in human cancer cells. In addition, the coding sequence of human SCA1 is not well defined. Therefore, only the expression of CD44 and ABCG2 markers were examined for MCF7 cells. 4T1 cells in the gel with elastic modulus of 5.3 kPa had the highest CD44 expression and lowest CD24 expression for all time points. CD44 expression of 4T1 and MCF7 cells initially increased and reached a maximum at day 8 for 2.5 and 5.3 kPa gels and at day 11 for 26.1 kPa gel. CD44 expression then decreased with incubation time. 4T1 and MCF7 cells encapsulated in the gels with moduli of 47.5 and 68.6 kPa did not show an increase in CD44 expression in 14 days. This biphasic marker expression with time was also observed for ABCG2 marker in 4T1 and MCF7 cells. At day 8, CD44 and ABCG2 expression of 4T1 cells increased by 2.2 and 1.8 folds, respectively, with increase in gel modulus from 2.5 to 5.3 kPa; those for MCF7 cells increased by 1.2 and 1.7 folds with increase in gel modulus from 25 to 5.3 kPa.

Figure 10:
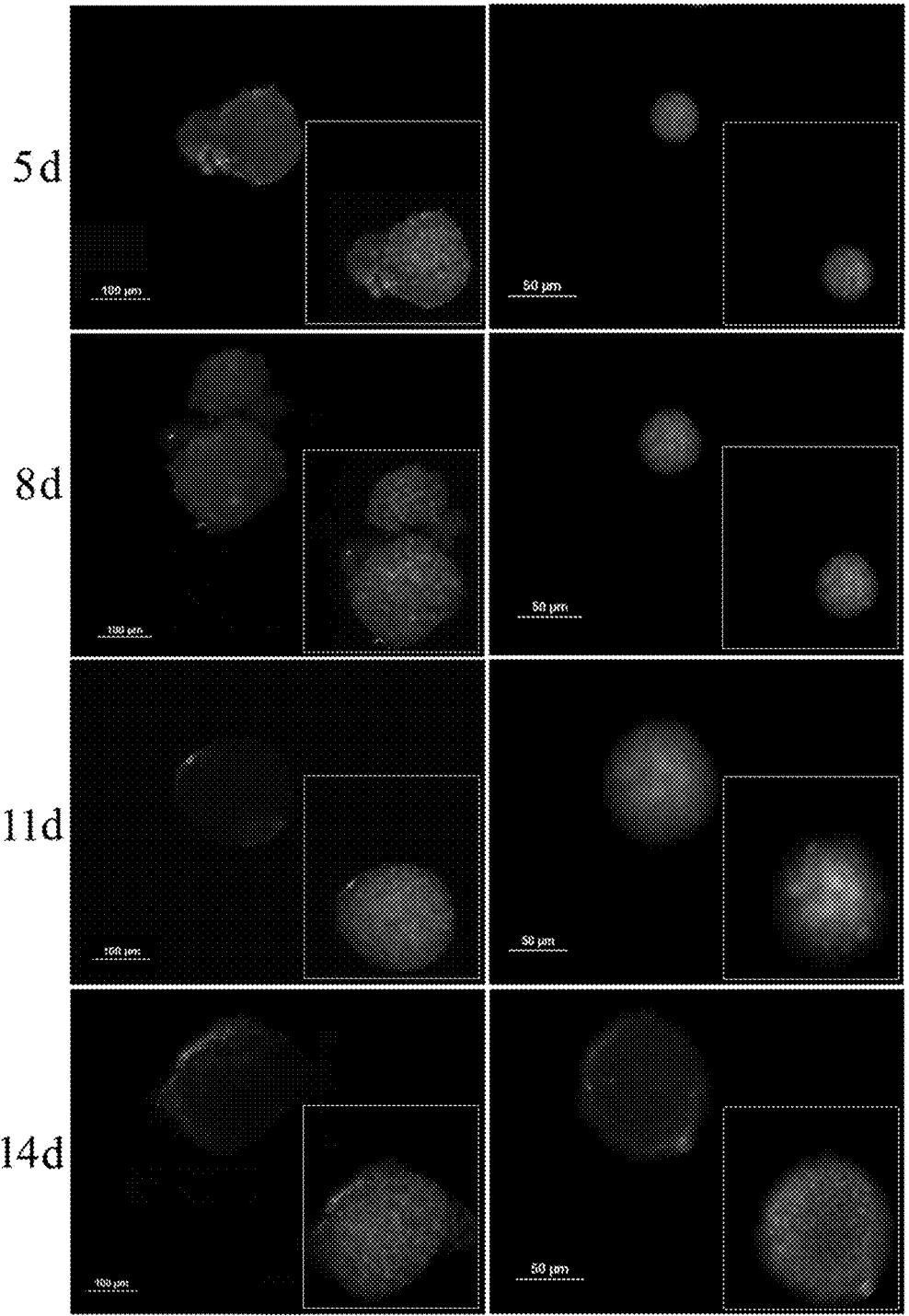
FIG. 10 illustrates the expression pattern of CD44 marker of 4T1 tumorspheres formed in suspension culture on low adhesion plates (column titled FIG. 10A) and formed by encapsulation in PEGDA hydrogel with 5.3 kPa elastic modulus (column titled FIG. 10B). Images in rows 1, 2, 3, and 4 are after 5, 8, 11, and 14 days of incubation, respectively. The cell nuclei were stained with DAPI.

To determine whether tumorspheres in the hydrogel had a higher level of stem cell population than those formed on ultra-low attachment plates, CD44 immunostaining of the 4T1 cells encapsulated in PEGDA gels (5.3 kPa modulus) was compared with those cultured on ultra-low attachment plates after 5, 8, and 11 days of culture, and the results are shown in FIG. 10. Tumorspheres grown in the gel and on ultra-low attachment plate both had high level of CD44 staining after 5 and 8 days of culture and the intensity of CD44 staining started to decrease after 8 days of culture for both groups. This was consistent with the CD44 mRNA data (see FIG. 9). However, tumorspheres grown in the gel had a more intense CD44 staining than those on ultra-low attachment plates for longer incubation times of 11 and 14 days, suggesting that the 3D microenvironment and gel stiffness modulated the maintenance of stemness in CSCs.

The results also show that 4T1 cells form higher number of tumorspheres when encapsulated in the PEG hydrogel compared to suspension cultures on low-adhesion plates. There are two possible explanations for this observation. One explanation is that the 3D hydrogel culture system more closely mimics the in vivo tissue environment than the suspension cultures with respect to the survival of CSCs. Evidence supporting this notion is that cancer cells have fewer number of cancer stem cells in 2D cultures than the in vivo. The elastic retractive force of the gel network can promote viability and proliferation of CSCs by enhancing FGF signaling and AKT activation. The other explanation is that the retractive force of the gel can induce the transformation of differentiated bulk cancer cells into CSCs. The transformation between CSCs and differentiated cancer cells is not unidirectional. Recent studies indicate that inducing epithelial to mesenchymal transition (EMT) is sufficient to transform a differentiated cancer cell into a CSC. In the process of EMT, tumor cells undergo cytoskeletal reorganization with subsequent changes in cell adhesion. At the molecular level, the key features of EMT include the altered expression of cell membrane proteins such as E-cadherin and β-catenin, and cell polarity. It is known that mechanical properties as well as biochemical composition in the tumor microenvironment play profound roles in EMT. It is possible that the hydrogel stiffness shifts the balance of EMT by regulating the conformation of cell membrane receptors and cell polarity. One example of such mechanism is EGFR signaling which has been associated with breast cancer stem cell maintenance. Compression of the cell membrane by the gel retractive force can shrink the interstitial space and increase the local ligand and receptor concentrations, thus increasing the autocrine EGFR signaling.

Example 2

Materials

Polyethylene glycol (PEG, nominal molecular weights 4.6 kDa), dichloromethane (DCM), N,N-dimethylformamide (DMF), diisopropylcarbodiimide (DIC), 4-dimethylaminopyridine (DMAP), trifluoroacetic acid (TFA), triisopropylsilane (TIPS), diethyl ether, and hexane were purchased from Acros (Fairfield, Ohio). The Rink Amide NovaGel™ resin, all Fmoc-protected amino acids, and hydroxybenzotriazole (HOBt) were purchased from Novabiochem (EMD Biosciences, San Diego, Calif.). Calcium hydride, triethylamine (TEA), paraformaldehyde, 4,6-diamidino-2-phenylindole (DAPI), insulin, penicillin, and streptomycin were purchased from Sigma-Aldrich (St. Louis, Mo.). Acetomethoxy derivative of calcein (cAM) and ethidium homodimer (EthD) were purchased from Molecular Probes (Life Technologies, Grand Island, N.Y.). Basic fibroblast growth factor (bFGF) and epidermal growth factor (EGF) were purchased from Lonza (Allendale, N.J.). Bovine serum albumin (BSA) was obtained from Jackson ImmunoResearch (West Grove, Pa.). Dulbecco's phosphate-buffer saline (PBS), trypsin-EDTA, RPMI-160 cell culture medium, fetal bovine serum (FBS), Alexa Fluor® 594 Phalloidin, and Quant-it PicoGreen dsDNA reagent kit were purchased from Invitrogen (Carlsbad, Calif.). Horse serum and DMEM-F12 medium were purchased from PAA Laboratories (Etobicoke, Ontario) and MediaTech (Manassas, Va.), respectively. Spectro/Por dialysis tube (molecular weight cutoff 3.5 kDa) was purchased from Spectrum Laboratories (Rancho Dominguez, Calif.). DCM was purified by distillation over calcium hydride. All other solvents were reagent grade and were used as received without further purification. The anti-Actin, anti-VEGFa and anti-Vimentin antibodies were purchased from Santa Cruz Biotechnology (Santa Cruz, Calif.). Fluorescent conjugated secondary antibodies were obtained from Invitrogen. 4T1 mouse breast carcinoma cell line was developed by Dr. Suzanne Ostrand-Rosenberg group and available from ATCC (Manassas, Va.). The cell line was characterized and purified by Dr. Ralph A. Reisfeld at the Scripps Research Institute (La Jolla, Calif.). 4T1 cells were a donation from Dr. Reisfeld under a Material Transfer Agreement. MCF7 human breast adenocarcinoma cell line and MCF10a non-tumorigenic epithelial cell line were obtained from ATCC.

Macromer Synthesis

The PEG gel was formed as described above. A hydrolytically degradable version of the PEGDA gel or poly (ethylene glycol-co-lactide) acrylate macromer (dPEGDA or LPELA) was also formed. In a first step, linear (LPEL) poly(ethylene glycol-co-lactide) macromers were synthesized by melt ring-opening polymerization of lactide with LPEG and SPEG, respectively, as polymerization initiators and TOC as the reaction catalyst. LPEG and SPEG were dried by azeotropic distillation from toluene prior to the reaction. The LA and PEG were added to a three-neck reaction flask equipped with an overhead stirrer. The LA:PEG molar ratio was varied from 0 to 20 to synthesize macromonomers with different lactide segment lengths. The reaction flask was heated to 120° C. with an oil bath under steady flow of dry nitrogen to melt the reactants. Next, 1 ml of TOC was added and the reaction was allowed to continue for 8 h at 135° C. After the reaction, the product was dissolved in DCM and precipitated in ice cold methanol followed by ether and hexane to fractionate and remove the unreacted monomer and initiator. The synthesized LPEL and SPEL macromers were vacuum-dried to remove any residual solvent and stored at −20° C. In the next step, the terminal hydroxyl groups of LPEL and SPEL macromers were reacted with acryloyl chloride to produce LPELA and SPELA macromonomers, respectively. Prior to the reaction, macromers were dissolved in DCM and dried by azeotropic distillation from toluene to remove residual moisture. After cooling under steady flow of nitrogen, the macromer was dissolved in DCM and the reaction flask was immersed in an ice bath. Equimolar amounts of acryloyl chloride and TEA were added drop-wise to the solution to limit the temperature rise of the exothermic reaction. The reaction was allowed to proceed for 12 h. After the reaction, solvent was removed by rotary evaporation, the residue was dissolved in ethyl acetate to precipitate the by-product triethylamine hydrochloride salt. Next, ethyl acetate was removed by vacuum distillation, the macromer was re-dissolved in DCM and precipitated twice in ice cold ethyl ether. The synthesized macromonomer was dissolved in DMSO and purified by dialysis to remove any unreacted acrylic acid. The LPELA and SPELA products were dried in vacuum to remove residual solvent and stored at −40° C.

Peptide Synthesis and Characterization

CD44 binding peptide (CD44BP), integrin-binding RGD peptide (IBP), and fibronectin-derived heparin-binding peptide (FHBP) as well as their mutants, were synthesized manually on Rink Amide resin in the solid phase using a known procedure. The sequences of these peptides and their mutants are listed in the table below.

| Peptide name | Sequence | Scrambled (mutant) |
| --- | --- | --- |
| CD44BP | RLVSYNGIIFFLK (SEQ ID NO: 17) | VLFGFLKIYSRIN (SEQ ID NO: 18) |
| IBP | GRGDS (SEQ ID NO: 19) | GRDGS (SEQ ID NO: 20) |
| FHBP | WQPPRARI (SEQ ID NO: 21) | RPQIPWAR (SEQ ID NO: 22) |

Briefly, the Fmoc-protected amino acid (6 eq.), DIC (6.6 eq.), and HOBt (12 eq.) were added to 100 mg resin and swelled in DMF (3 mL). Next, 0.2 mL of 0.05 M DMAP was added to the mixture and the coupling reaction was allowed to proceed for 4-6 h at 30° C. with orbital shaking. The resin was tested for the presence of unreacted amines using the Kaiser reagent. If the test was positive, the coupling reaction was repeated. Otherwise, the resin was treated with 20% piperidine in DMF (2×15 min) and the next Fmoc-protected amino acid was coupled using the same procedure. After coupling the last amino acid, the peptides were functionalized with an acrylamide group directly on the peptidyl resin by coupling acrylic acid to the N-terminal amine group under conditions used for the amino acid coupling reaction. The acrylamide-terminated peptide was cleaved from the resin by treating with 95% TFA/2.5% TIPS/2.5% water and precipitated in cold ether. The acrylamide-terminated (Ac) peptides were further purified by preparative HPLC on a 250×10 mm, 10 µm Xterra Prep RP18 column (Waters, Milford, Mass.) with a flow rate of 2 mL/min using a gradient 5-95% MeCN in 0.1% aqueous TFA at detection wavelength of 214 nm. The HPLC fraction was lyophilized and the product was characterized with a Finnigan 4500 Electro Spray Ionization (ESI) spectrometer (Thermo Electron, Waltham, Mass.).

Hydrogel Synthesis and Measurement of Modulus

The PEGDA macromer was crosslinked in aqueous solution to form a gel by ultraviolet (UV) initiated radical polymerization with 4-(2-hydroxyethoxy)phenyl-(2-hydroxy-2-propyl) ketone (Irgacure 2959; CIBA, Tarrytown, N.Y.) photoinitiator. Five mg of initiator was dissolved in 1 mL PBS at 50° C. The macromer was dissolved in PBS by vortexing and heating to 50° C. To prepare 10% PEGDA hydrogel precursor solution, 30 mg PEGDA macromer was mixed with 270 mL of the initiator solution. The hydrogel precursor solution was degassed and transferred to a Teflon mold (5 cm×3 cm×500 µm), covered with a transparent glass plate and fastened with clips. Then, the assembly was irradiated with a BLAK-RAY 100-W mercury long wavelength (365 nm) UV lamp (Model B100-AP; UVP, Upland, Calif.) for 10 min. Next, disc shape samples were cut from the gel using an 8 mm cork borer and swollen in PBS for 24 h at 37° C. To measure the elastic modulus of the gel, samples were loaded on the Peltier plate of a rheometer (TA Instruments, New Castle, Del.) and subjected to uniaxial compressive force at a displacement rate of 7.5 µm/s. The slope of the linear fit to the stress-strain curve for 5-10% strain was taken as the elastic modulus (E) of the gel.

Cancer Stem Cell Culture and Cell Encapsulation in the Hydrogel

The tumor cells were cultured in RMPI-1640 medium with 10% FBS under 5% $CO_2$ at 37° C. Cells were trypsinized after reaching 70% confluency. The synthesized acrylamide-terminated peptides were added to the PEGDA macromer solution and the mixture was sterilized by filtration (220 nm filter). Next, $1.4 \times 10^5$/ml cells (4T1, MCF7, or MCF10a) were added to the macromer solution and mixed gently with a pre-sterilized glass rod. The cell-suspended hydrogel precursor solution was crosslinked with UV for 10 min as described above. After cross-linking, the gel was cut into disks and incubated in stem cell culture medium on ultra-low attachment tissue culture plates under 5% $CO_2$. The stem cell medium consisted of DMEM-F12 supplemented with 0.4% BSA, 5 µg/ml insulin, 40 ng/ml bFGF, 20 ng/ml EGF, 5% horse serum, 100 U/ml penicillin, and 100 µg/ml streptomycin. For growing tumorspheres in suspension, trypsinized cells (4T1 or MCF7) were cultured on ultra-low attachment tissue culture plates with stem cell culture medium under 5% $CO_2$ at 37° C.

Cell Imaging and Determination of Cell Number

To determine cell viability, gels were stained with cAM and EthD dyes after cell encapsulation to image live and dead cells, respectively. Stained samples were imaged with an inverted fluorescent microscope (Nikon Eclipse Ti-ε, Nikon, Melville, N.Y.). Cell viability was quantified by dividing the image into smaller squares and counting the number of live and dead cells manually. At each time point, three gel samples were removed from the culture medium and stained for imaging. For imaging the encapsulated cells, gels were rinsed twice with PBS and fixed with 4% paraformaldehyde for 3 h. After fixation, cells were permeabilized using PBS containing 0.1% Triton X-100 for 5 min. After rinsing, cells were incubated with Alexa 488 phalloidin (1:200 dilution) and DAPI (1:5000 dilution) to stain actin filaments of the cell cytoskeleton and cell nuclei, respectively. Stained samples were imaged with a Nikon Eclipse Ti-ε inverted fluorescent microscope. For determination of cell number, the gel samples were homogenized, cells were lysed, and aliquots were used to measure the double stranded DNA (dsDNA) content using a Quant-it PicoGreen assay. Briefly, an aliquot (100 µL) of the working solution was added to 100 µL of the cell lysate and incubated for 4 min at ambient conditions. The fluorescence of the solution was measured with a plate reader (Synergy HT, Bio-Tek, Winooski, Vt.) at emission and excitation wavelength of 485 and 528 nm, respectively. Measured fluorescent intensities were correlated to cell numbers using a calibration curve constructed with cells of known concentration ranging from zero to $10^5$ cells/m L.

Real Time PCR Analysis

Total cellular RNA of the gel samples was isolated using TRIzol (Invitrogen). 250 ng of the extracted purified RNA was reverse transcribed to cDNA by SuperScript II Reverse Transcriptase (Invitrogen) with the random primers. The obtained cDNA was subjected to real time quantitative polymerase chain reaction (RT-qPCR) amplification with the appropriate gene specific primers. RT-qPCR was performed to analyze the differential expression of CSC markers CD44, CD24, ABCG2, and SCA1 genes with SYBR green Real-MasterMix (Eppendorf, Hamburg, Germany) using Bio-Rad iCycler PCR system (Bio-Rad, Hercules, Calif.). The expression level of GAPDH gene was used as an internal control. The primers for real time PCR were designed by Primer 3 software. The forward and reverse primer sequences, listed in the table below, were synthesized by Integrated DNA technologies (Coralville, Iowa). The relative gene expression levels were quantified by the $2^\wedge(-\Delta\Delta CT)$ method. Briefly, $\Delta CT$ was calculated as $\Delta CT = CT^{target\ gene} - CT^{GAPDH}$. $\Delta\Delta CT$ of the target gene was calculated as $\Delta\Delta CT = \Delta CT^{experimental\ group} - \Delta CT^{reference\ group}$. The reference was the first time point (right after cells were encapsulated in the gel). The relative gene expression (fold-change compared to the reference time point) was calculated as $2^\wedge(-\Delta\Delta CT)$.

| PCR Primer | Forward | Reverse |
|---|---|---|
| mouse GAPDH | 5'-CATGGCCTTCCG TGTTCCTA-3' (SEQ ID NO: 1) | 5'-CCTGCTTCACCA CCTTCTTGA-3' (SEQ ID NO: 2) |
| mouse CD44 | 5'-GAA TGTAACCT GCCGCTACG-3' (SEQ ID NO: 3) | 5'-GGAGGTGTTGGA CGTGAC-3' (SEQ ID NO: 4) |
| mouse CD24 | 5'-CTTCTGGCACTG CTCCTACC-3' (SEQ ID NO: 5) | 5'-GAGAGAGAGCCA GGAGACCA-3' (SEQ ID NO: 6) |
| mouse ABCG2 | 5'-AGCAGCAAGGAA AGATCCAA-3' (SEQ ID NO: 7) | 5'-GGAATACCGAGG CTGATGAA-3' (SEQ ID NO: 8) |
| mouse SCA1 | 5'-TGGACACTTCTC ACACTA-3' (SEQ ID NO: 9) | 5'-CAGAGCAAGAGG GTCTGCAGGAG-3' (SEQ ID NO: 10) |
| mouse E-Cadherin | 5'-ACTGTGAAGGGA CGGTCAAC-3' (SEQ ID NO: 32) | 5'-GGAGCAGCAGGA TCAGAATC-3' (SEQ ID NO: 23) |
| mouse N-Cadherin | 5-GGGACAGGAACAC TGCAAAT-3' (SEQ ID NO: 24) | 5-CGGTTGATGGTCC AGTTTCT-3' (SEQ ID NO: 25) |
| mouse integrin αV | 5'-GCTTAAAGGCAG ATGGCAAC-3' (SEQ ID NO: 26) | 5'-AAATGGTGATGG GAGTGAGC-3' (SEQ ID NO: 27) |
| mouse integrin β3 | 5'-TGACATCGAGCA GGTGAAAG-3' (SEQ ID NO: 28) | 5'-GAGTAGCAAGGC CAATGAGC-3' (SEQ ID NO: 29) |
| mouse EGFR | 5'-CAGTGGGCAACC CTGAGTAT-3' (SEQ ID NO: 30) | 5'-GGGCCCTTAAAT ATGCCATT-3' (SEQ ID NO: 31) |
| human GAPDH | 5'-GAGTCAACGGAT TTGGTCGT-3' (SEQ ID NO: 11) | 5'-TTGATTTTGGAG GGATCTCG-3' (SEQ ID NO: 12) |
| human CD44 | 5'-GGCTTTCAATAG CACCTTGC-3' (SEQ ID NO: 13) | 5'-ACACCCCTGTGT TGTTTGCT-3' (SEQ ID NO: 14) |
| human ABCG2 | 5'-CACCTTATTGGC CTCAGGAA-3' (SEQ ID NO: 15) | 5'-CCTGCTTGGAAG GCTCTATG-3' (SEQ ID NO: 16) |

Flow Cytometry Analysis

Cells encapsulated in the gel were fixed with 4% paraformaldehyde for 30 min followed by washing with PBS. Next, the gel was incubated in oxidative degradation solution (0.1M CoCl in 20% hydrogen peroxide). After the gel was degraded, cells were washed three times with cold PBS containing 5% BSA. MCF7 cells were incubated with phycoerythrin (PE) mouse anti-human CD24 and fluorescein isothiocyanate (FITC) mouse anti-human CD44 (BD Biosciences, Franklin Lakes, N.J.), and 4T1 cells were incubated with PE-anti-mouse CD24 and FITC-anti-mouse CD44 (eBioscience, San Diego, Calif.) in 100 µl PBS with 5% BSA for 45 min on ice in the dark. Cells were then washed with cold PBS with 5% BSA three times and analyzed by a flow cytometer (FC500, Beckman Coulter, Brea, Calif.). Flow cytometry was done multiple times on each sample to ascertain reproducibility of the results.

Western Blot

The cell encapsulated gel was washed with PBS and homogenized in RIPA buffer (1% NP40, 1% SDS, 150 mM NaCl, 20 mM Tris-CI pH7.4, 1 mM EDTA protease inhibitors) to extract the proteins. The homogenized sample was centrifuged for 5 min to isolate total proteins. Next, proteins were separated by standard SDS-PAGE using Mini-gel system (Bio-Rad) and transferred to a nitrocellulose membrane by the semi-dry transfer apparatus (Bio-Rad). Membranes were incubated in the blocking buffer (5% fat-free dry milk in TBST buffer) at ambient conditions for 1 h followed by incubation with primary antibodies (1:200-1:2000) overnight at 4° C. After washing, the membrane was incubated with HRP-conjugated secondary antibodies for 1 h at ambient conditions. After extensive washing with TBST, the membrane was incubated with ECL detection reagents and exposed to an X-ray film. The intensity of the band was quantified with the Image-J software (National Institutes of Health, Bethesda, Md.).

Tumor Growth In Vivo and Measurement

To test tumor formation ability of 4T1 cells in the hydrogel, the cell encapsulated gels were cultured in vitro in the stem cell medium for 9 days as described above. After tumorsphere formation, gel pieces containing $1 \times 10^5$ tumorsphere cells were implanted subcutaneously in syngeneic Balb/C mice (6 mice/group). Groups included 4T1 tumorsphere cells, grown on ultra-low attachment plates, and injected subcutaneously (control group), degradable version of the PEGDA gel (dPEGDA) without tumor cells (control group), 4T1 cells encapsulated in the dPEGDA and cultured in vitro for 9 days prior to implantation, and 4T1 cells encapsulated in CD44BP-conjugated dPEGDA gel and cultured in vitro for 9 days prior to implantation. When tumors became measurable, tumor size and growth rate were measured and calculated. Mice were euthanized when tumor volume reached above 1000 mm$^3$ or 4 weeks after inoculation.

Statistical Analysis

Data were expressed as means±standard deviation. Significant differences between groups were evaluated using a two-way ANOVA with replication test followed by a two-tailed Student's t-test. To account for multiple pair comparisons, p-values from the t-test were corrected using False Discovery Rate (FDR) method. A value of p<0.05 was considered statistically significant.

Sphere Formation in PEGDA Hydrogel

Figure 11:
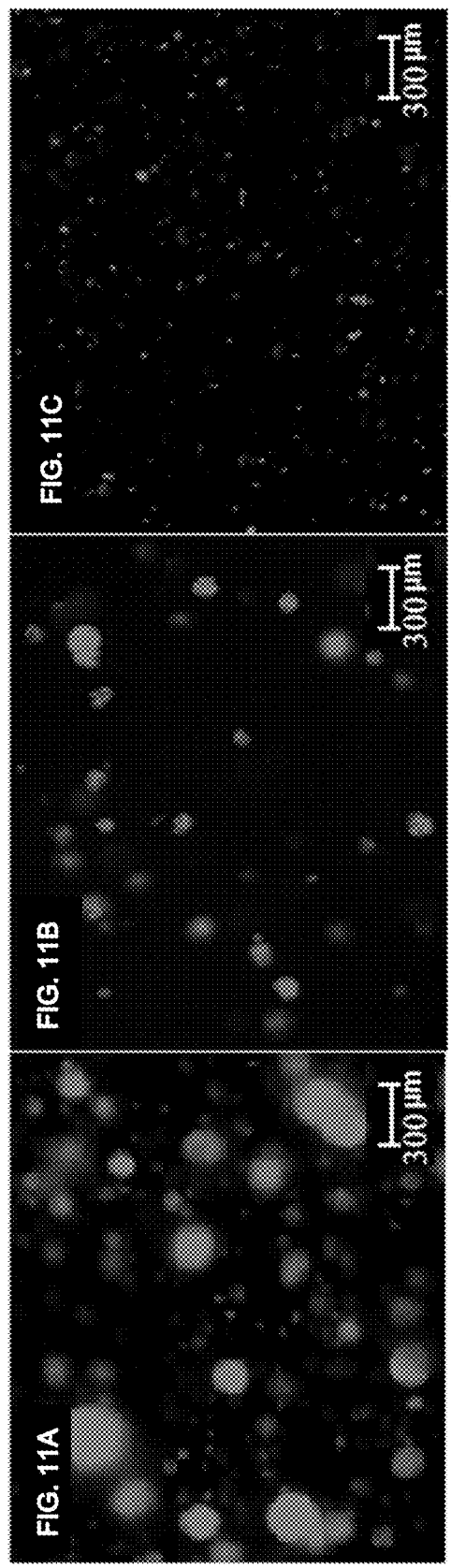
FIG. 11 illustrates sphere formation and the effect of cell type encapsulated in PEGDA gels on the expression of CSC markers. Representative fluorescent images of the tumorsphere size and distribution for 4T1 (FIG. 11A), MCF7 (FIG. 11B), and MCF10a (FIG. 11C) cells encapsulated in PEGDA gels ($1.4 \times 10^5$ cells/ml), and cultured in stem cell culture medium. Encapsulated cells were stained with phalloidin for cytoskeleton and DAPI for nucleus. Also shown is the effect of cell type on cell number density (FIG. 11D) and tumorsphere diameter (FIG. 11E) for tumor cells encapsulated in PEGDA hydrogel and incubated in stem cell culture medium for 6 or 9 days. The sphere size distribution (FIG. 11F) was determined 9 days after encapsulation. Effect of cell type on CD44 (FIG. 11G), CD24 (FIG. 11H) and ABCG2 (FIG. 11I) mRNA marker expression for tumor cells encapsulated in PEGDA hydrogel and incubated in stem cell culture medium for 6 or 9 days. RNA levels of the cells were normalized to those at time zero. A star indicates a statistically significant difference (p<0.05) between the test group and the groups with different cell type in the same time point (the same diameter range in f). Values are expressed as mean±SD (n=3).
Figure 11:
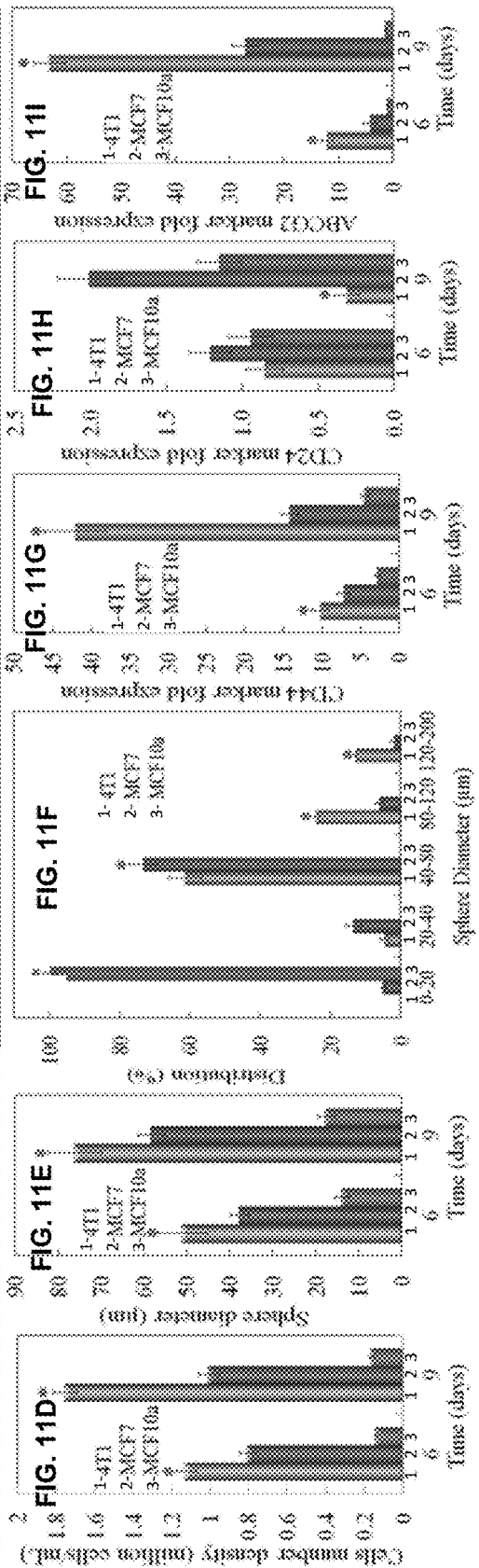

Fluorescent images in FIG. 11A, FIG. 11B, and FIG. 11C show that 4T1 and MCF7 cancer cells encapsulated in the gel formed spheres but not the normal MCF10a cells, suggesting that the spheres originated from the CSC subpopulation of 4T1 and MCF7 cancer cells. The cell number density, sphere size, and size distribution for 4T1, MCF7 and MCF10a cells encapsulated in the gel after 6 and 9 days incubation in stem cell culture medium are shown in FIG. 11D through FIG. 11F. The cell density of 4T1 and MCF7 cells significantly increased for both time points, while that of MCF10a remained at a low level (FIG. 11D), suggesting that the PEGDA gel promoted the proliferation of tumor cells, but not the normal cells. The density of 4T1 tumorspheres was slightly higher than that of MCF7 after 6 or 9 days of incubation. 4T1 cells also formed larger spheres than MCF7 as shown in FIG. 11E. After 9 days of culturing in the gel, nearly 40% of the 4T1 spheres were larger than 80 μm while most of the MCF7 spheres were between 40 and 80 μm (FIG. 11F). MCF10a remained as single cells in the gel with size smaller than 20 μm.

The expressions of breast CSC markers CD44, CD24, and ABCG2 for the encapsulated cells are shown in FIG. 11G through FIG. 11I, respectively. After 6 days of incubation, CD44 expression level in 4T1 and MCF7 cells increased by 10 fold of the initial level (FIG. 11G). CD44 expression was further increased in 4T1 cells 9 days after encapsulation. However, as reported previously, the expression of CD44 in 4T1 and MCF7 cells started to decrease after 11 days of incubation irrespective of the extent of cell viability and the increase in tumorsphere size. The expression of CD24 RNA was significantly reduced in 4T1 cells but increased slightly in MCF7 (FIG. 11H). Although CD44+/CD24− cells are considered breast CSCs, the expression of CD24 as a CSC marker in MCF7 is not conclusive. Previous studies have indicated that CD44+/CD24− and CD44+/CD24+ cells both display CSC phenotypes in MCF7 cells. The discrepancy may be due to different primers used for real time PCR quantification, and antibodies used for cell sorting as well as the methods used for analysis. The expression of ABCG2, a subunit of ABC transporter that is responsible for the drug resistance of CSCs was also increased in 4T1 and MCF7 cells (FIG. 11I). On the other hand, the expression of these markers in MCF10a cells did not change.

Figure 12:
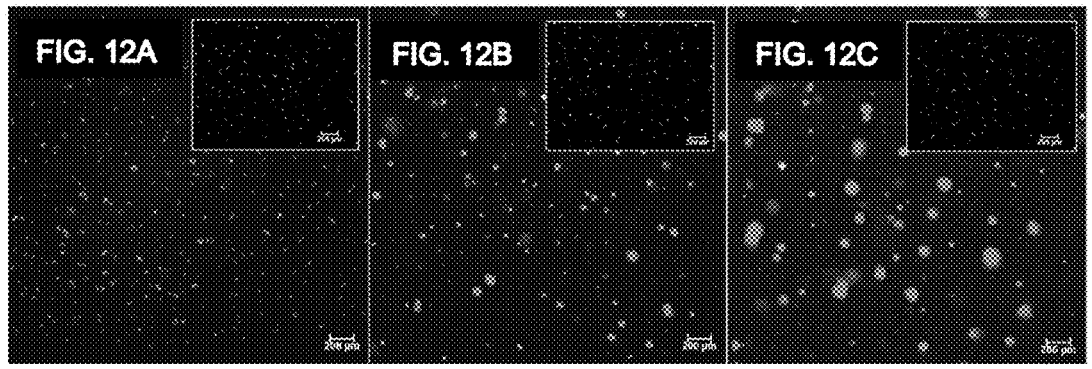
FIG. 12 illustrates viability of cells encapsulated in PEGDA gel and includes representative images of live and dead 4T1 cells encapsulated in PEGDA gels with 5 kPa modulus and cultured in stem cell culture medium for 2 (FIG. 12A), 6 (FIG. 12B) and 12 (FIG. 12C) days. Cells were stained with cAM/EthD for live and dead cell imaging. The insets in FIG. 12A, FIG. 12B, and FIG. 12C are live/dead images of 4T1 cells in PEGDA gels with 70 kPa modulus after 2, 6, and 12 days, respectively.

FIG. 12A, FIG. 12B and FIG. 12C show representative images of live and dead 4T1 cells encapsulated in PEGDA gels with 5 kPa modulus after 2 (FIG. 12A), 6 (FIG. 12B) and 12 (FIG. 12C) days, respectively. The insets are the corresponding figures in the 70 kPa gel. For 5 kPa gel, cell viability after 2, 6, and 12 days increased from 91±3% to 94±4% and 97±2%, respectively. For the high modulus 70 kPa gel, no tumorsphere formed and cell viability decreased from 89±4% at day 2 to 84±3% and 78±2% at days 6 and 12, respectively. Based on these results, the effect of peptide conjugation on tumorsphere formation was investigated with 4T1 cells in the PEGDA gel with 5 kPa modulus and incubation time of 9 days.

Figure 13:
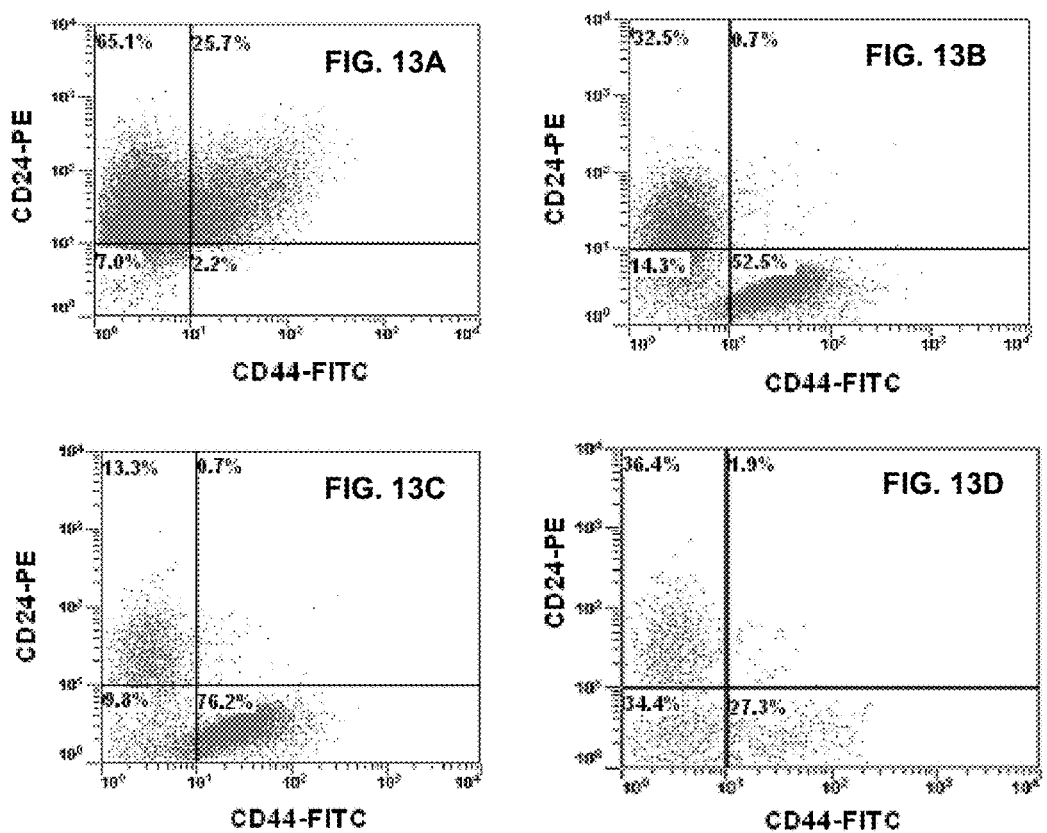
FIG. 13 illustrates CSC population in the cells encapsulated in PEGDA gel. MCF7 cells were encapsulated in PEGDA gels with 5 kPa modulus and cultured in stem cell culture medium. Cells before encapsulation (FIG. 13A), 3 days (FIG. 13B), 8 days (FIG. 13C) and 11 days (FIG. 13D) after encapsulation were stained with CD44-FITC and CD24-PE antibodies. The population of CD24+, CD44+ and CD44+/CD24− cells was determined by flow cytometry. Flow cytometry was repeated multiple times on each sample to ascertain reproducibility of the results.

The CD44+/CD24− marker expression is widely used for identification of breast CSCs. Flow cytometry analysis of MCF7 cells isolated from the gel is shown in FIG. 13. The percentage of CD44+/CD24− cells before encapsulation in the gel was 2% (FIG. 13A) but it increased to 53% (FIG. 13B) and 76% (FIG. 13C) after 3 and 8 days incubation in the gel, respectively. However, the percent CD44+/CD24− cells decreased to 27% after 11 days incubation in the gel (FIG. 13D). These results are consistent with previous results in which the CD44 mRNA expression of 4T1 and MCF7 cells initially increased with time, then began to decrease after 14 days of incubation in the gel. The flow cytometry results demonstrate that the percentage of CSCs in the population of cells encapsulated in the gel increased dramatically after 8 days with incubation time and tumorsphere formation. Since the percentage of live cells in the gel increased with incubation time (see FIG. 12), the decrease in the percentage of CSCs at day 11 (FIG. 13D) was presumably due to the differentiation of CSCs.

Effect of CD44 Binding Peptide on Tumorsphere Formation in Hydrogels

Figure 14:
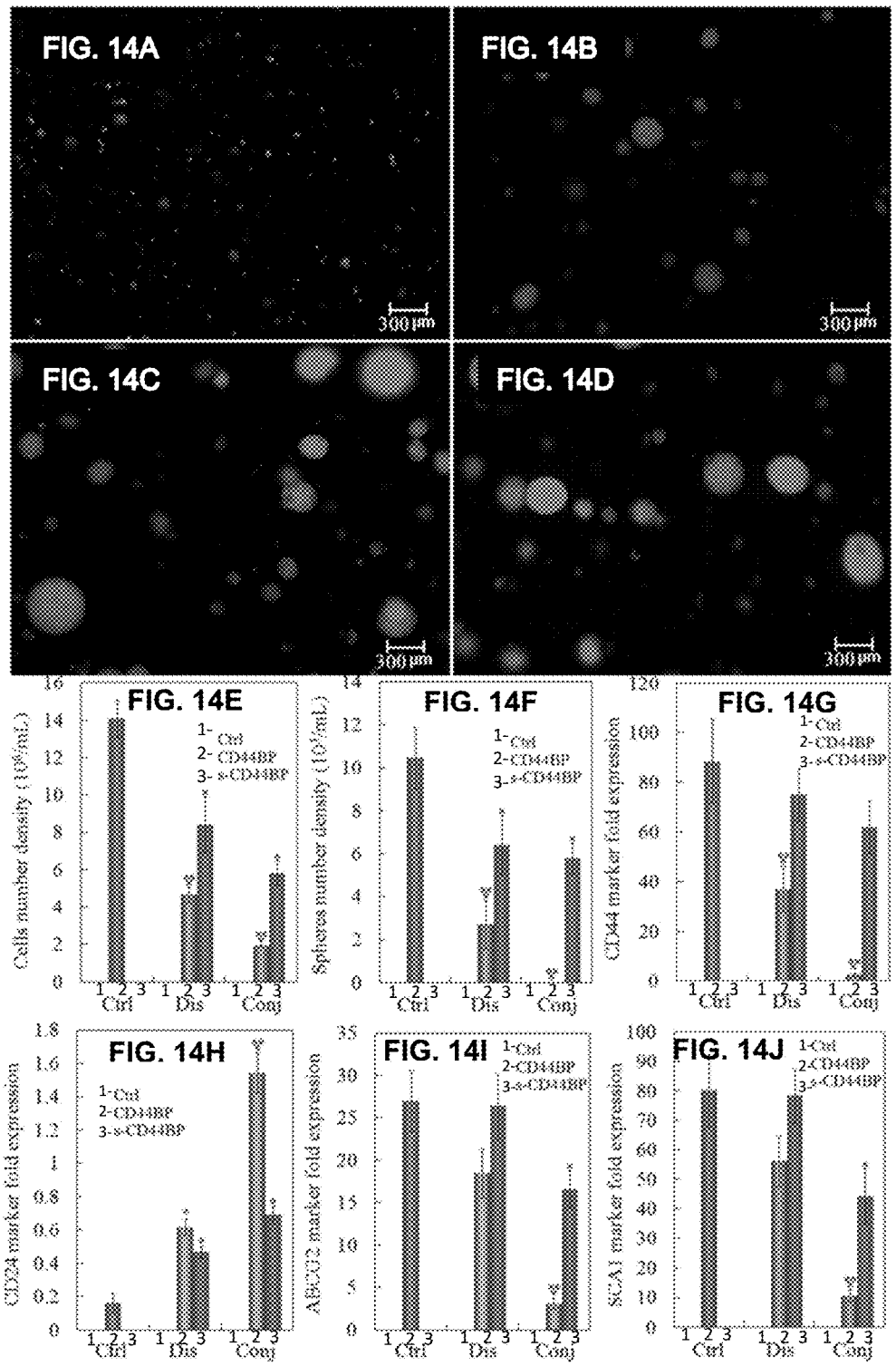
FIG. 14 illustrates the effect of CD44BP on tumorsphere formation and CSC marker expression. Representative fluorescent images of the tumorsphere size and distribution for 4T1 cells encapsulated in PEGDA gels ($1.4 \times 10^5$ cells/ml) conjugated with CD44BP (FIG. 14A, conj CD44BP), conjugated with a scrambled sequence of CD44BP (FIG. 14B, conj s-CD44BP), CD44BP dissolved in the gel (FIG. 14C, dis CD44BP), and s-CD44BP dissolved in the gel (FIG. 14D, dis s-CD44BP) and cultured in the stem cell culture medium for 9 days. Effect of CD44BP on cell number density (FIG. 14E) and tumorsphere number density (FIG. 14F) for 4T1 tumor cells encapsulated in PEGDA hydrogel and incubated in the stem cell culture medium for 9 days. Effect of CD44BP conjugation on CD44 (FIG. 14G), CD24 (FIG. 14H), ABCG2 (FIG. 14I) and SCA1 (FIG. 14J) mRNA marker expression for 4T1 tumor cells encapsulated in PEGDA gel and incubated in the stem cell culture medium for 9 days. RNA levels of the cells were normalized to those at time zero. A star indicates a statistically significant difference (p<0.05) between the test group and "Ctrl". Two stars indicates a significant difference (p<0.05) between the two CD44BP and s-CD44BP groups within the same form of peptide addition (Dis or Conj). Values are expressed as mean±SD (n=3).

Groups included the PEGDA gel without peptide conjugation (control, labeled as Ctrl in FIG. 14), the gel with CD44BP or scrambled CD44BP (FIG. 14, s-CD44BP) dissolved in the gel and in the culture medium to maintain constant peptide concentration (labeled as Dis in FIG. 14), and the gel with CD44BP or s-CD44BP conjugated to the gel (covalent attachment, labeled as Conj in FIG. 14). Fluorescent images FIG. 14A through FIG. 14D show the tumorspheres formed in conj CD44BP, conj s-CD44BP, dis CD44BP, and dis s-CD44BP, respectively. Tumorsphere formation was abolished when 4T1 cells were encapsulated in the CD44BP conjugated gel, indicating the importance of CD44 signaling in the maintenance of CSCs. The effect of CD44BP was consistent with previous reports. However, CD44BP dissolved in the gel (FIG. 14C and FIG. 14D) did not inhibit sphere formation. These results suggested that CD44BP did not function as a soluble chemokine to inhibit CSC proliferation but functioned within the insoluble part of the ECM. The effect of a scrambled CD44BP (s-CD44BP) was also tested. Conjugated or dissolved s-CD44BP had no significant effect on tumorsphere formation, indicating that bioactivity was specific to CD44BP.

FIG. 14E and FIG. 14F show the effect of CD44BP on cell number density and sphere size of 4T1 cells encapsulated in the gel after 9 days of incubation. The 4T1 cell density in the gel reached $14 \times 10^6$/mL after 9 days with $1.4 \times 10^5$/mL initial cell seeding in the gel. The density of 4T1 cells in the gel with CD44BP (conjugated or dissolved and with or without mutation) were lower compared with the gel without any peptide. However, cells in the conj CD44BP gel had the strongest effect on cell density and completely abolished sphere formation (FIG. 14A). The expression of CSC markers, CD44, CD24, ABCG2 and SCA1 was also determined and the results are shown in FIG. 14G through FIG. 14J, respectively. 4T1 cells in the CD44BP gel that formed spheres (conj s-CD44BP, dis CD44BP and dis s-CD44BP) had high expressions of CD44, ABCG2 and SCA1 and low expression of CD24. On the other hand, cells in the conj CD44BP gel, which did not form tumorspheres, had decreased expressions of CD44, ABCG2 and SCA1, and increased expression of CD24. These results indicated that tumorsphere formation by 4T1 cells in the gel correlated with the CSC population.

Effect of CD44 Binding Peptide on Tumor Formation In Vivo

Figure 15:
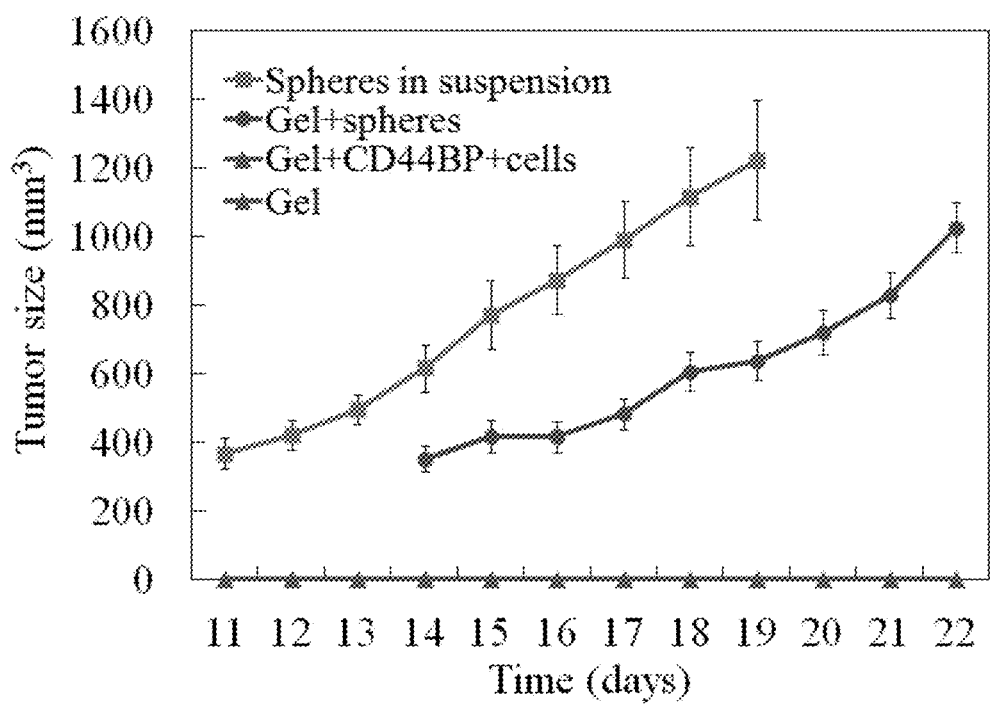
FIG. 15 illustrates the effect of CD44BP conjugated to the gel on tumor formation in vivo. The gel without cell (negative control, triangle), 4T1 tumorspheres in suspension (positive control, square), 4T1 cells encapsulated in the gel without CD44BP (circle), and 4T1 cells encapsulated in the gel with CD44BP (triangle) were inoculated subcutaneously in syngeneic Balb/C mice. Tumor sizes were measured daily from post-inoculation day 11 (n=6/group). Tumor growth was not observed in the negative control group (the gel without cell) and the group with 4T1 cells in the gel with CD44BP (the lines for these two groups are overlapped in the figure).

It is well established that tumor growth in vivo requires a permissive environment that can support vascularization and matrix remodeling. Therefore, a degradable version of PEGDA gel (dPEGDA) was used to investigate the effect of CD44BP conjugated to the gel on tumor formation in vivo by the encapsulated 4T1 cells. Groups included 4T1 tumorspheres injected directly without the gel, gels without cell, gels without peptide conjugation but with 4T1 tumorspheres, and gels with 4T1 cells conjugated with CD44BP. The gels without cell did not from a visible tumor after 4 weeks (FIG. 15). Tumors became measurable after 10 days with direct subcutaneous injection of 4T1 tumorspheres. 4T1 tumorspheres in the gel without CD44BP conjugation also formed a tumor after 13 days of inoculation. Even though the formation of tumor was delayed when cells were encapsulated in the gel, the growth rate (the slop of the tumor size curve) did not differ significantly between the group with 4T1 in PBS and 4T1 in the gel (FIG. 15). The observed lag time in tumor formation for the encapsulated cancer cells is presumably related to the degradation time of the gel and connection of the tumor cells to the surrounding tissue. However, 4T1 cells encapsulated in the conj CD44BP gel did not form a visible tumor after 4 weeks of inoculation, indicating that CD44BP conjugated to the gel inhibited tumor formation in vivo.

Figure 16:
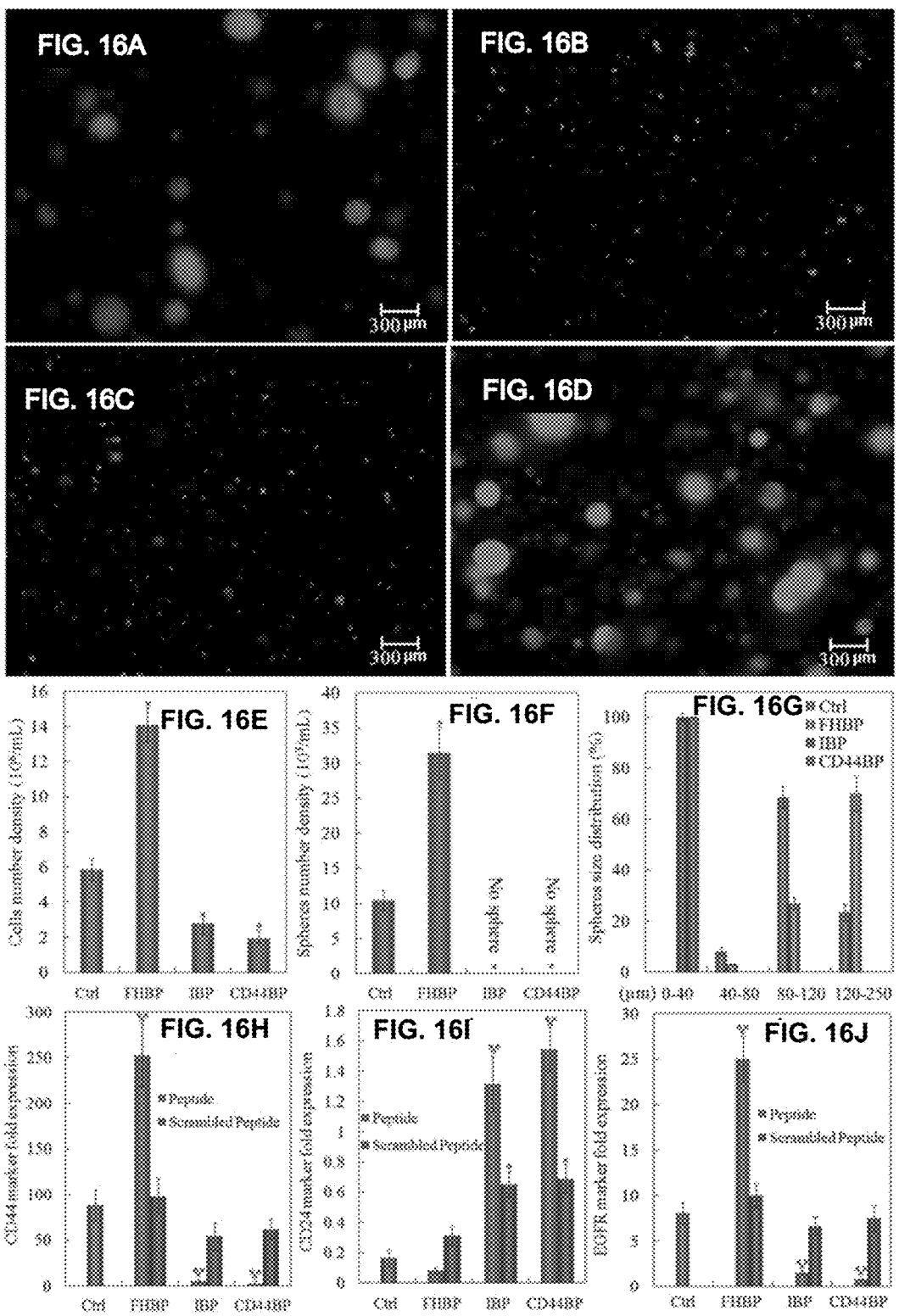
FIG. 16 illustrates the comparison of tumorsphere formation in PEGDA gels conjugated with CD44BP, IBP, or FHBP. Representative fluorescent images of the tumorsphere size and distribution for 4T1 cells encapsulated in PEGDA gels ($1.4 \times 10^5$ cells/ml) without peptide conjugation (FIG. 16A), conjugation with CD44BP (CD44BP, FIG. 16B), conjugation with RGD integrin-binding peptide (IBP, FIG. 16C) and conjugation with fibronectin-derived binding peptide (FHBP, FIG. 16D) and cultured in the stem cell culture medium for 9 days. Effect of cell binding peptide on cell number density (FIG. 16E), tumorsphere number density (FIG. 16F) and sphere size distribution (FIG. 16G) for 4T1 tumor cells encapsulated in PEGDA gel and incubated in the stem cell culture medium for 9 days. Effect of cell binding peptide on CD44 (FIG. 16H), CD24 (FIG. 16I) and EGFR (FIG. 16J) mRNA marker expression for 4T1 tumor cells encapsulated in PEGDA hydrogel and incubated in the stem cell culture medium for 9 days. RNA levels of the cells were normalized to those at time zero. A star indicates a statistically significant difference (p<0.05) between the test group and "Ctrl". Two stars indicates a significant difference (p<0.05) between the wild type and scrambled peptides for the same conjugated peptide. Values are expressed as mean±SD (n=3).

Comparing the Effect of CD44 Binding Peptide on Tumorsphere Formation with Integrin and Heparin Binding Peptides The effect of CD44BP on tumorsphere formation in the gel prompted testing of other cell-binding peptides. IBP, an integrin receptor binding peptide and FHBP, a heparin-binding domain of fibronectin that binds to cell surface heparin sulfate proteoglycans, were conjugated to the gel. Groups included 4T1 cell seeded gel without peptide conjugation, the cell-seeded gel with CD44BP conjugation, the cell-seeded gel with IBP conjugation, and the cell-seeded gel with FHBP conjugation. For determination of marker expression, gels conjugated with a scrambled sequence of the peptides were also tested. Fluorescent images in FIG. 16A through FIG. 16D show sphere formation by 4T1 cells in the gels without peptide, with conj CD44BP, conj IBP, and conj FHBP, respectively. The IBP conjugation, similar to CD44BP, abolished 4T1 tumorsphere formation in the gel (FIG. 16C). However, tumorsphere formation increased when 4T1 cells were encapsulated in the FHBP conjugated gel (FIG. 16D). Further characterization of the cells in these gels (FIG. 16E through FIG. 16G) showed that the cells in IBP and CD44BP conjugated gels had reduced cell number, did not form sphere, and remained as single cells or small cell aggregates (<25 μm). On the other hand, the cells in FHBP conjugated gel had higher cell number and larger spheres compared with those in the gels without peptide conjugation.

To determine whether the size and number density of tumorspheres in the gel correlated with the CSC sub-population, CD44 and CD24 expression of the cells in the peptide-conjugated gels were measured. 4T1 cells in the gels without any peptide conjugation and with FHBP conjugation had elevated expression of CD44 marker while the cells in gels conjugated with CD44BP or IBP had decreased CD44 expression (see FIG. 16H). More importantly, the CD44 expression in the cells encapsulated in FHBP conjugated gel was significantly higher than that without peptide conjugation. The expression of CD24 in those gels had an opposite pattern to that of CD44 (see FIG. 16I). In breast cancer, the expression of epidermal growth factor receptor (EGFR) is also closely related to the maintenance of CSCs. The expression of EGFR marker by 4T1 cells encapsulated in the peptide-conjugated gels is shown in FIG. 16J. Similar to CD44 marker, the expression of EGFR was increased in the cells encapsulated in FHBP conjugated gel but decreased in CD44BP and IBP conjugated gels. Furthermore, conjugation of a mutant sequence of the peptides to the gel had insignificant or limited effect on tumorsphere formation and the expression of CSC markers, compared to the wild type (FIG. 16H through FIG. 16J).

Figure 17:
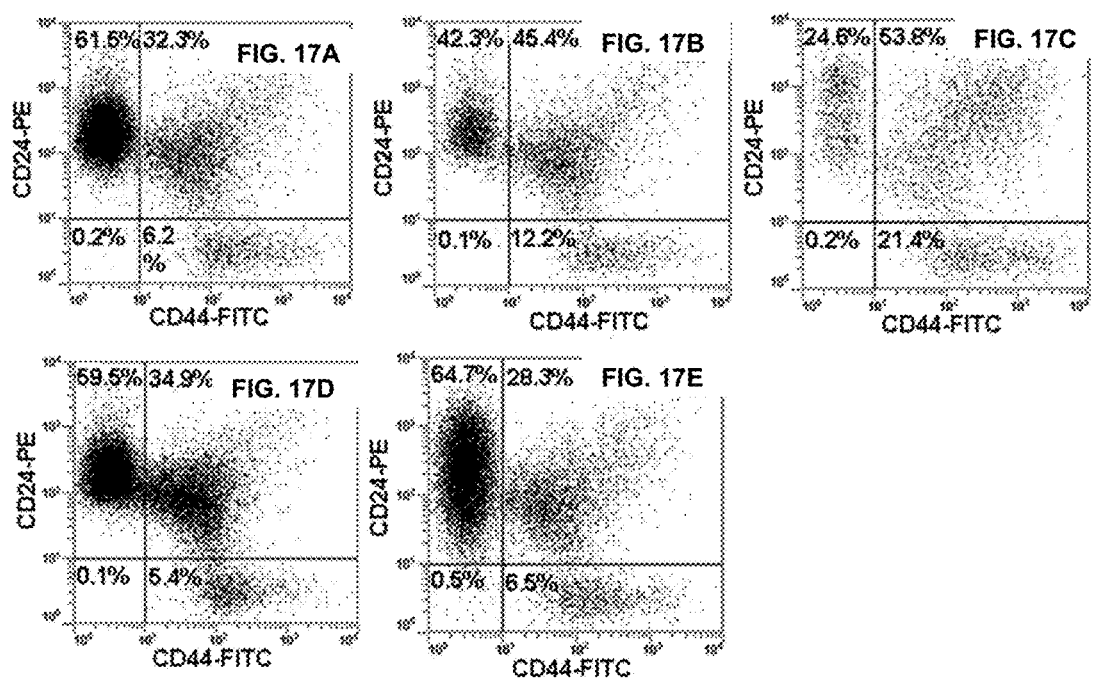
FIG. 17 illustrates CSC population in cells encapsulated in PEGDA gels conjugated with CD44BP, IBP, or FHBP. 4T1 cells were encapsulated in PEGDA gels with 5 kPa modulus and cultured in stem cell culture medium. Cells before encapsulation (FIG. 17A), 9 days after encapsulation in the gel without peptide (FIG. 17B), 9 days in the gel conjugated with FHBP (FIG. 17C), 9 days in the gel conjugated with IBP (FIG. 17D), and 9 days in the gel conjugated with CD44BP were stained with CD44-FITC and CD24-PE antibodies (FIG. 17E). The population of CD24+, CD44+ and CD44+/CD24− cells was determined by flow cytometry. Flow cytometry was repeated multiple times on each sample to ascertain reproducibility of the results.

The effect of cell binding peptides on CSC sub-population was further examined in 4T1 cells by flow cytometry. The percentage of CD44+/CD24− cells in 4T1 cells cultured without gel encapsulation was about 6% (FIG. 17A). This percentage doubled to 12% for cells encapsulated in the PEGDA gel without peptide conjugation (FIG. 17B). When 4T1 cells were encapsulated in the gel conjugated with FHBP, the sub-population of CD44+/CD24− cells was further increased to about 21% (FIG. 17C). Conversely, the fraction of CSC sub-population in the gel decreased to the original level (5.4% for IBP and 6.5% for CD44BP) when 4T1 cells were encapsulated in the gels conjugated with IBP (FIG. 17D) or CD44BP (FIG. 17E) that inhibited sphere formation. These results suggested that tumorsphere formation by 4T1 cells in the gel was related to the CSC sub-population.

Effects of Cell Binding Peptides on the Expression of Other CSC Related Markers

Figure 18:
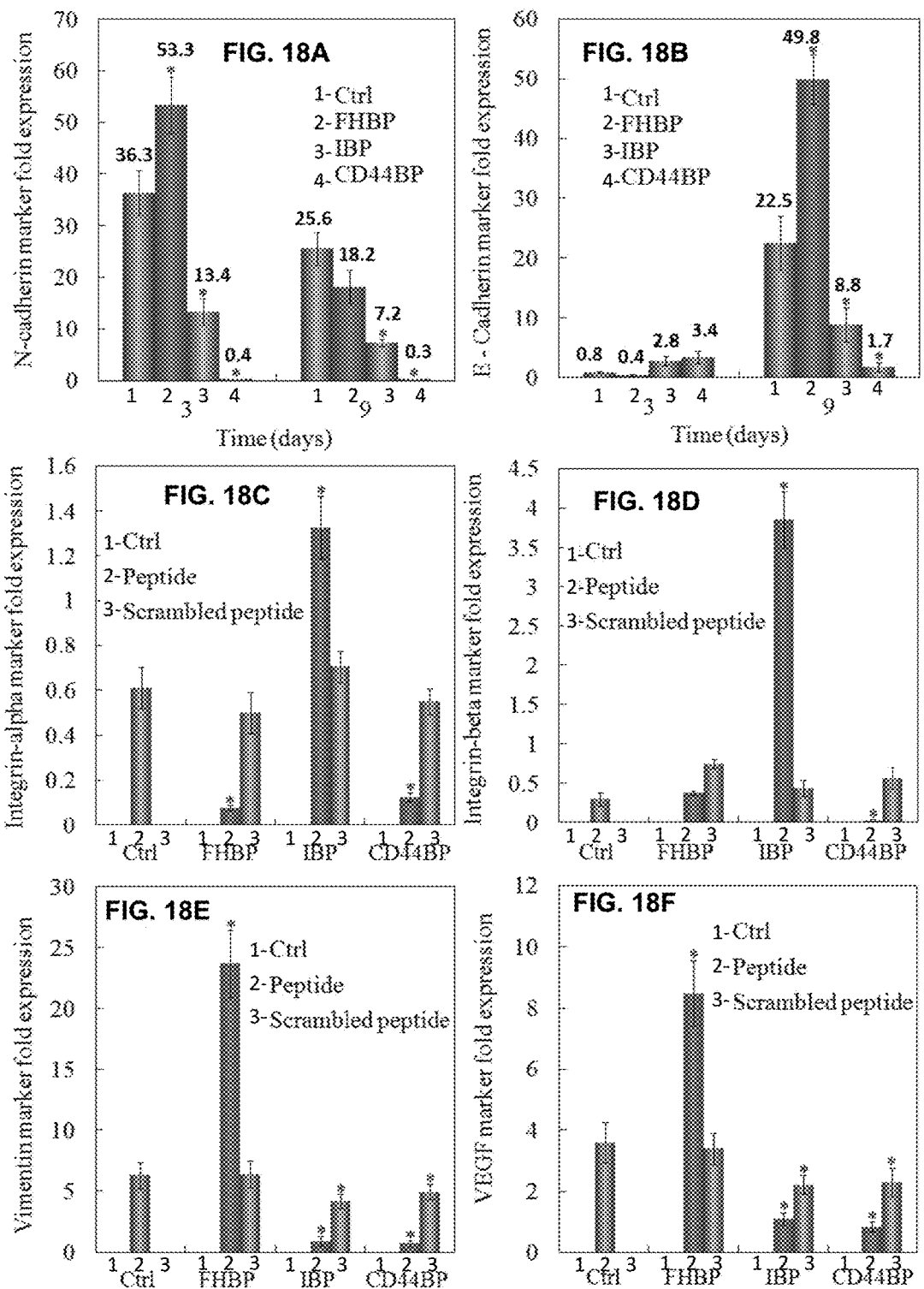
FIG. 18 illustrates expression of the markers related to CSC maintenance in cells grown in the gel conjugated with CD44BP, IBP, or FHBP. Effect of cell binding peptide on N-Cadherin (FIG. 18A), E-Cadherin, (FIG. 18B), integrin αV (FIG. 18C), and integrin β3 (FIG. 18D) mRNA marker expression for 4T1 tumor cells encapsulated in the PEGDA hydrogel and incubated in the stem cell culture medium for 9 days. Effect of cell binding peptide on vimentin (FIG. 18E) and VEGF (FIG. 18F) protein expression. The protein expression was determined by western blot and quantified with imageJ. Actin was used as the internal control and the protein expressions were normalized to those at time zero. RNA levels of the cells were normalized to those at time zero. A star indicates a statistically significant difference ($p<0.05$) between the test group and "Ctrl". Values are expressed as mean±SD (n=3).

One of the pathways to transform differentiated cancer cells into CSCs is epithelial to mesenchymal transition (EMT). The hallmark of EMT is the decreased expression of E-Cadherin and increased expression of N-Cadherin. The expressions of E-Cadherin and N-Cadherin 3 and 9 days after cells were encapsulated in the peptide-conjugated gels are shown in FIG. 18A and FIG. 18B, respectively. At the early time point (3 days), the expression of E-Cadherin was decreased while the expression of N-Cadherin was increased in the gel with FHBP, suggesting that EMT was a possible mechanism for the enhanced tumorsphere formation in the gel. However, at the later time point (9 days), the expression of E-Cadherin in the cells grown in FHBP gel was much higher than that in other groups. This was probably due to sphere formation in the FHBP gel. E-Cadherin is a cell adhesion protein and its expression increases with increased cell-cell interaction. Consistent with that, cells in the IBP and CD44BP gels, which did not form spheres, had low expressions of E-Cadherin (FIG. 18B).

The importance of integrins in cancer and CSC maintenance is well known. Since RGD is an integrin binding peptide, we examined the expression of integrin αV and β3, two integrin subunits required for RGD binding, and the expressions are shown in FIG. 18C and FIG. 18D, respectively. The expression of integrin αV and β3 was reduced in cells grown in FHBP and CD44BP gels, even though the cells in FHBP gel formed spheres while those in CD44BP gel did not. Interestingly, the expression of integrin αV and β3 was significantly increased in the cells in IBP gel. It is possible that blocking integrin signaling by RGD activates a feedback loop to induce integrin expression. These results suggest that the expression of integrin does not correlate directly with tumorsphere formation or CSC maintenance of 4T1 cells. Conjugation of a mutant sequence of the peptides to the gel had limited effect on the expression of CSC markers, indicating that the effect was specific to the wild type.

The expression of vimentin and VEGF, two other markers related to invasive breast cancer and CSC maintenance, was also determined at the protein level, as shown in FIG. 18E and FIG. 18F. The expression of vimentin and VEGF was high in cells that formed spheres, and their expression correlated with the sphere size and number (FIG. 16E, FIG. 16F).

In this study, we found that CD44BP inhibits tumorsphere formation only when conjugated (covalently attached) to the gel. Dissolving the peptide in the gel or in the medium did not have an effect on tumorsphere formation. This result suggests that CD44BP does not act as a soluble chemokine to block or activate CD44 signaling. We speculate that CD44BP induces a conformational change in CD44 receptor through a mechanism like receptor clustering.

Using the 3D PEGDA matrix with a certain stiffness, it has been demonstrated that the cell adhesion CD44 binding peptide (CD44BP), RGD integrin binding peptide (IBP), and fibronectin-derived heparin binding peptide (FHBP) can be individually conjugated to the inert PEGDA gel and their effect on the maintenance of breast cancer stem cells can be investigated without the interference of other factors. The CD44BP and IBP conjugated to the inert gel completely abolished tumorsphere formation by the encapsulated 4T1 breast cancer cells while FHBP enhanced tumorsphere formation compared to those without peptide. The inert 3D hydrogel cell culture system provides a novel tool to investigate the individual effect of factors in the microenvironment on maintenance of CSCs without the interference of other factors. More specifically, the 3D hydrogel cell culture system can be used to selectively enrich the cancer cells with CSC sub-population for instance for the purpose of testing toxicity of chemotherapy agents against the CSC sub-population.

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure which is defined in the following claims and all equivalents thereto. Further, it is identified that many embodiments may be conceived that do not achieve all of the advantages of some embodiments, yet the absence of a particular advantage shall not be construed to necessarily mean that such an embodiment is outside the scope of the present invention.

---

What is claimed is:

1. A three dimensional hydrogel matrix comprising a crosslinked inert gel that is absent of ligands that can interact with cell surface receptors, the crosslinked inert gel comprising crosslinked inert polyethylene glycol diacrylate homopolymer, the hydrogel matrix further comprising a peptide conjugated to the crosslinked inert gel, the three dimensional hydrogel matrix having an elastic modulus of from 2 kilopascals to 70 kilopascals.

2. The three dimensional hydrogel matrix of claim 1, wherein the three dimensional hydrogel matrix has an elastic modulus of from about 2.5 kilopascals to about 10 kilopascals.

3. The three dimensional hydrogel matrix of claim 1, the peptide affecting the growth, development, and/or proliferation of a cancer stem cell.

4. The three dimensional hydrogel matrix of claim 1, wherein the peptide comprises a CD44 binding peptide or a mutant thereof, an integrin binding peptide or a mutant thereof, or a heparin binding peptide or a mutant thereof.

5. The three dimensional hydrogel matrix of claim 1, wherein the peptide comprises RLVSYNGIIFFLK (SEQ ID NO: 17), VLFGFLKIYSRIN (SEQ ID NO: 18), GRGDS (SEQ ID NO: 19), GRDGS (SEQ ID NO: 20), WQPPRARI (SEQ ID NO: 21), or RPQIPWAR (SEQ ID NO: 22).

6. The three dimensional hydrogel matrix of claim 1 further comprising a biochemical factor incorporated in the three dimensional hydrogel matrix.

7. The three dimensional hydrogel matrix of claim 1, further comprising a population of cells encapsulated in the matrix.

8. The three dimensional hydrogel matrix of claim 7, the population of cells comprising cancer stem cells.

9. The three dimensional hydrogel matrix of claim 8, the population of cells further comprising differentiated cancer cells.

10. The three dimensional hydrogel matrix of claim 9, the differentiated cancer cells comprising breast cancer cells.

11. The three dimensional hydrogel matrix of claim 7, the population of cells further comprising tumor stroma cells.

12. The three dimensional hydrogel matrix of claim 1, the hydrogel matrix further comprising a crosslink initiator.

13. A method for studying a cell population, the method comprising:
  encapsulating a cell population in the three dimensional hydrogel matrix of claim 1; and
  incubating the three dimensional hydrogel matrix encapsulating the cell population in a cell culture medium, the cell culture medium comprising a biochemical factor.

14. The method of claim 13, wherein the biochemical factor is a cancer drug.

15. The method of claim 13, wherein the peptide is a CD44 binding peptide or a mutant thereof, an integrin binding peptide or a mutant thereof, or a heparin binding peptide or a mutant thereof.

16. The method of claim 15, wherein the peptide is RLVSYNGIIFFLK (SEQ ID NO: 17), VLFGFLKIYSRIN (SEQ ID NO: 18), GRGDS (SEQ ID NO: 19), GRDGS (SEQ ID NO: 20), WQPPRARI (SEQ ID NO: 21), or RPQIPWAR (SEQ ID NO: 22).

17. The method of claim 13, the cell population comprising cancer stem cells and/or differentiated cancer cells.

18. The method of claim 13, the cell population comprising tumor stroma cells.

* * * * *